United States Patent
Phaneuf et al.

(10) Patent No.: US 7,413,575 B2
(45) Date of Patent: Aug. 19, 2008

(54) NANOFIBROUS BIOCOMPOSITE PROSTHETIC VASCULAR GRAFT

(76) Inventors: Matthew D. Phaneuf, 29 Oak Ridge La., Ashland, MA (US) 01721; Philip J. Brown, 105 Lighthouse Dr., Williamston, SC (US) 29697; Martin J. Bide, 658 Rose Hill Rd., South Kingstown, RI (US) 02879

( * ) Notice: Subject to any disclaimer, the term of this patent is extended or adjusted under 35 U.S.C. 154(b) by 240 days.

(21) Appl. No.: 11/211,935

(22) Filed: Aug. 25, 2005

(65) Prior Publication Data

US 2006/0129234 A1 Jun. 15, 2006

Related U.S. Application Data

(60) Provisional application No. 60/605,628, filed on Aug. 30, 2004.

(51) Int. Cl.
*A61F 2/06* (2006.01)
*B29C 47/00* (2006.01)
*H05B 7/00* (2006.01)

(52) U.S. Cl. .................................... 623/1.54; 264/465
(58) Field of Classification Search ............... 623/1.42, 623/1.43, 1.47, 1.49, 1.51, 1.54, 1.53; 977/743; 264/465; 139/387 R
See application file for complete search history.

(56) References Cited

U.S. PATENT DOCUMENTS

| 6,626,939 | B1 * | 9/2003 | Burnside et al. | 623/1.38 |
| 6,713,011 | B2 * | 3/2004 | Chu et al. | 264/465 |
| 7,056,339 | B2 * | 6/2006 | Elkins et al. | 623/1.46 |
| 2002/0090725 | A1 * | 7/2002 | Simpson et al. | 435/402 |
| 2003/0215624 | A1 * | 11/2003 | Layman et al. | 428/221 |
| 2004/0199241 | A1 * | 10/2004 | Gravett et al. | 623/1.13 |

* cited by examiner

*Primary Examiner*—Thomas J Sweet
*Assistant Examiner*—Jonathan R Stroud
(74) *Attorney, Agent, or Firm*—David Prashker, Esq.

(57) ABSTRACT

The present invention provides a bioactive, small-diameter (typically less than 6 mm in internal diameter) vascular graft prosthesis, and is a textile conduit preferably manufactured using a novel electrospinning perfusion methodology. One preferred embodiment is a nanofibrous biocomposite textile conduit which comprises a prepared liquid admixture of polyester (Dacron), a biodurable implantable synthetic polymer, and Type IV collagen, an extracellular matrix protein. This prepared admixture and blending of diverse fibrous matter is utilized in a novel electrospinning perfusion process to form a small-diameter (less than 6 mm) fabricated textile conduit, a discrete article of manufacture, which then serves as an antecedent tangible workpiece for a subsequently-made prosthetic vascular graft construct.

42 Claims, 14 Drawing Sheets

NANOFIBROUS BIOCOMPOSITE PROSTHETIC VASCULAR GRAFT

PRIORITY CLAIM

The present invention was first filed on Aug. $30^{th}$, 2004 as U.S. Provisional Patent Application No. 60/605,628. The priority and legal benefit of this first filing is expressly claimed.

FIELD OF THE INVENTION

The present invention is concerned generally with vascular prostheses; and is particularly directed to the manufacture and use in-vivo of a nanofibrous vascular prosthesis (especially having channels less than 6 mm internal diameter size) that is capable of emulating the biological and physical properties of the native blood vessel wall.

BACKGROUND OF THE INVENTION

The replacement of segments of human blood vessels with synthetic vascular grafts is well accepted practice in the medical arts; and vascular graft prostheses comprised of synthetic materials are commonly used for the replacement of segments of human blood vessels. Synthetic vascular grafts presently exist in a wide variety of dimensions and configurations, and are formed as substrates from many different kinds of materials.

Historical Development

Over the last 40 years, considerable progress has been made in the development of arterial and venous prostheses. The modern era of vascular surgery began in the early 1950's, about forty years after Carrel and Gutherie (1906) demonstrated that autologous or naturally occurring veins could be used to replace native arteries. Subsequently, with the advent of antibiotics and anticoagulants in ancillary medicine, the development of autologous vascular grafts prospered. Also at that time, the reversed saphenous vein was considered the best autologous graft for artery replacement; and this vein was used successfully in femoral artery replacement by Kunlin in 1949.

However, the need for smaller diameter vascular prostheses led to further research by Gross and associates involving homografts of sterilized tissue. Although early results were encouraging, the long-term results were still unsatisfactory, with the grafts often failing due to thrombosis and aneurysm.

Then, Voorhees made an important observation in 1952 that changed the direction of vascular graft development. After discovering that cells grew on silk thread after exposure to blood, Vorhees then showed the effectiveness of synthetic textile or fabric tubes as arterial graft replacements. With these pioneer events, a new era of vascular surgery began; and the search for the most suitable substrate material and optimal structure for a synthetic textile graft began. As the last fifty years have shown, a host of diverse approaches, and developments have come into existence—including even those conducted recently, which have investigated different substrate and structural variations such as knitted or woven textiles, fabrics with larger or smaller pores, material substrates with diverse surface finishes and coatings, and the techniques of crimping, compacting, and structural reinforcements.

Current Medical Practices

Among the clinically accepted and currently successful vascular grafts are those substrates formed using a biologically compatible material which is fashioned into tubular shapes and which retain an open internal lumen for blood to flow normally through the graft after its implantation in-vivo. Some of these biologically compatible substrate materials include thermoplastics such as polyester, polytetrafluoroethylene (PTFE), silicone and polyurethanes. Among the most widely used thermoplastic materials are polyester fibers and expanded-PTFE. The polyester fibers in particular may be knitted or woven into a textile or fabric; and the polymers may be fashioned as a monofilament, a multifilament or staple yarn, or a combination of each of these.

Selection of a particular type of vascular graft substrate by a surgeon depends upon several factors. Among these deciding factors is the particular anatomic location intended for the graft's implantation. The intended anatomic location in-vivo also dictates and controls the inner and outer diameter size of the vascular graft, which must maintain a sufficiently large or small lumen to accommodate a normal blood flow rate in the region of implantation. The ultimate strength requirements and the typical blood pressure demands for the graft at the intended anatomic site of implantation will also affect the graft substrate selection.

In general, the woven or knitted types of vascular graft provide a greater strength and a reduced porosity for the substrate, but these types of graft materials are considered to be more difficult to handle and to suture into proper place. Velours are often preferred as a substrate material because the velour surfaces facilitate subsequent in-vivo growth of tissue into the loops extending from the surface of the velour fabric. The knitted types of grafts are typically softer and more easily sutured into place, but are usually more porous substrates. Also, depending on the intended anatomic location of the implant in-vivo and the quantity of heparin then circulating in the blood of the patient (the "heparinization condition"), synthetic fabric vascular grafts generally must be preclotted with the patient's own blood before implantation in-vivo. In comparison, pre-clotting with the patient's own blood may not be essential with a woven type of graft substrate, but is medically recommended nonetheless.

Some Illustrative Examples of Conventionally Available Vascular Grafts

Composition and Manner of Construction

Synthetic fabric vascular grafts may be of a woven or knitted form—with or without a velour construction. A synthetic vascular graft having a warp-knit construction is disclosed by U.S. Pat. No. 3,945,052. Another type of vascular graft having a warp knit double-velour construction is described by U.S. Pat. No. 4,047,252; and a synthetic, woven, double-velour graft where the velour loops are formed of preshrunk multifilament warp yams is described by U.S. Pat. No. 4,517,687.

Similarly, U.S. Pat. No. 4,892,539 describes a synthetic fabric woven graft with single velour on the outer surface. The graft is described as woven from multifilament polyester yarns, specifically described as texturized, with the single outer velour formed of filling yams with each velour loop extending outside a plurality of warp yams.

A representative showing of more recent developments in synthetic fabric graft constructions are disclosed by U.S. Pat. Nos. 6,077,297; 5,935,161; 5,891,193; 5,509,931; 5,496,364; 5,487,858; 5,385,580; 5,282,848; 5,197,976; 5,192,310; 5,178,630; and 4,842,575. All of these are individually expressly incorporated by reference herein.

Compacting and Crimping

After knitting or weaving one or more yams into a tubular form, the fabric grafts are then typically compacted using a method such as is disclosed by U.S. Pat. Nos. 3,853,462 and 3,986,828. Compaction results in the shrinking of the yarns comprising the graft article and generally reduces the overall porosity of the fabric substrate. Typically, these tubular graft constructions have an inner diameter size from about 6 mm to 40 mm after compacting.

Subsequent to compacting, the synthetic tubular grafts are usually crimped on the exterior surface. The act of crimping involves forming ridges in the tubular wall of the fabric grafts to eliminate the dangers of a kinking or a collapse of the tubing when the graft is flexed; and crimping results in the formation of uniform, regular, circular corrugations of the tubular wall, which maintains uniform strength over the entire exterior surface of the graft tube.

Crimping is typically applied to both the woven and knit fabric vascular graft articles. Representative examples are shown by U.S. Pat. No. 3,878,565, which describes a graft body which is crimped into irregular, circumferential corrugations. Note however, that the degree of protection afforded by irregular corrugation varies over the lengths of the tube and can fall below a required level of protection at specific regions. For example, the warp-knit and woven grafts described above in U.S. Pat. Nos. 3,945,052, 4,047,252 and 4,517,687 are circularly crimped; and the graft in U.S. Pat. No. 4,892,539 is crimped in a spiral fashion. Such crimped or corrugated walls can disrupt blood flow and create areas of thick tissue buildup, due to the wall surface profile; and a number of crimping methods which avoid such undesirable disruptive effects have come into existence [see for example U.S. Pat. Nos. 3,304,557; 3,479,670; and 3,272,204 respectively].

Porosity

An important factor in the selection of a particular graft substrate is the porosity of the fabric wall of which the graft is formed. Porosity is a significant parameter because it controls the tendency to hemorrhage during and after implantation of the graft in-vivo; and also controls the subsequent ingrowth of tissue over time into the wall of the implanted graft. It is thus desirable that the material substance of the vascular graft be sufficiently blood-tight to prevent the loss of blood during the surgical implantation procedure; nevertheless, the graft wall structure must be sufficiently porous to allow for the subsequent ingrowth of fibroblast and smooth muscle cells when attaching the graft article to the vascular system of the host.

Synthetic vascular grafts such as are described in U.S. Pat. Nos. 3,805,301 and 4,047,252 are elongated flexible tubular bodies formed of a fiber such as Dacron. In the '301 patent, the graft article is a warp knitted tube, while in the '252 patent it is a double-velour synthetic graft. Both of these types of grafts have a sufficiently porous structure to permit ingrowth of host cells and tissue. Note also that the general procedure for implantation includes the step of pre-clotting, wherein the graft is immersed in the blood of the patient and allowed to stand for a period of time sufficient for clotting to occur. After pre-clotting, hemorrhaging does not occur when the graft is implanted and growth of tissue is not impeded. However, it is desirable to avoid pre-clotting as it takes valuable time during surgery.

More recent developments concerning porosity and its effects upon vascular prostheses are disclosed by U.S. Pat. Nos. 6,702,848; 6,616,699; 6,540,780; and 5,462,704 respectively. All of these are expressly incorporated by reference herein.

Collagen Containing Vascular Grafts

Blood-tight absorbable collagen reinforced grafts have been proposed [see U.S. Pat. No. 3,272,204]. The type of collagen disclosed by the '204 patent is obtained from the deep flexor tendon of cattle. Tendon-derived collagen is generally highly cross-linked and difficult to process by the enzyme digestion procedure described in the patent.

An additional reinforced vascular prosthesis is described by U.S. Pat. No. 3,479,670 which discloses an open mesh cylindrical tube wrapped by an outer helical wrapping of fused polypropylene mono-filament which may be filled with collagen fibrils to render the prosthesis impermeable to bacteria and fluids. Note also that the collagen fibrils utilized are the same as described in U.S. Pat. No. 3,272,204.

More recent developments concerning collagen and its effects upon vascular graft prostheses are described by U.S. Pat. Nos. 6,165,489; 6,162,247; 5,851,230; and 5,108,424 respectively. All of these are individually expressly incorporated by reference herein.

PTFE Grafts

Tubular vascular grafts of smaller inner diameter (for example, 6 mm inner diameter or less) are often utilized in peripheral regions of the body and appendages. Today, the most successful grafts of small diameter are those grafts comprised of polytetrafluoroethylene (or PTFE), one specific type of TEFLON polymer [see for example, U.S. Pat. Nos. 4,187,390 and 3,953,566 respectively]. These PTFE grafts are usually formed by an extrusion of the PTFE material, and can exist in both original (non-expanded) PTFE and expanded PTFE chemical formulations. While accepted for medical use in small diameter applications, PTFE graft constructions often require surgical replacement within relatively short periods of time compared to the larger diameter fabric vascular grafts described above.

A wide range and variety of different PTFE chemical formulations and compositions, methods of manufacture, and fabrication formats are commonly known and used today. Merely exemplifying the diversity of these PTFE materials and modes of fabrication are: The laminated self-sealing vascular access graft of U.S. Pat. No. 6,319,279; the PTFE vascular graft and method of manufacture described by U.S. Pat. No. 6,719,783; and the self-sealing PTFE vascular graft and manufacturing methods recited by U.S. Pat. No. 6,428,571. In addition, a varied range of structural modifications differing in fibril length, wall thickness, external wraps, and ring supports, internal coatings, and prosthesis size and shape are presently known. See for example, U.S. Pat. Nos. 4,082,893; 4,177,334; 4,250,138; 4,304,010; 4,385,093; 4,478,898; 4,482,516; 4,743,480; 4,816,338; 4,478,898; 4,619,641; and 5,192,310. Accordingly, the text of each of these issued patents, as well as their internally cited publications, is expressly incorporated by reference herein.

Dacron Grafts

'DACRON" or polyethylene terephthalate fibers and fabrics, have been used as one of the original materials for prosthetic grafts (see for example, U.S. Pat. Nos. 3,945,052; 4,047,252; 4,082,507; 4,130,904; 4,164,045; 4,167,045; 4,286,341; and 4,355,426). The use of polyethylene terephthalate fibers and fabrics continues today, with particular emphasis upon their presence either as one component fiber which is intermingled and combined with other kinds of fibers, or as a reinforcing netting structural material which is typically employed as one layer of matter in a multi-laminate layered construction (see for example, U.S. Pat. Nos. 6,689, 162; 6,503,273; and 6,440,166).

Alternative Biocompatible Substrate Materials for Vascular Grafts

The presently available compositions which may be used as the substrate material of a vascular graft, however, is not confined or limited to the use of PTFE (in any of its conventionally known chemical formulations) or polyethylene terephthalate (DACRON) fibers and fabrics. To the contrary, a variety of different alternative graft materials are presently available. Among these alternative materials are: multi-layered and self-sealing polyurethane (manufactured by Thoratec, Pleasanton, Calif.); bioartificial matter derived from mesenteric vein (Hancock Jaffee Laboratories inc., Irvine, Calif.); and a cryopreserved allograft material in which cellular elements have been removed using antigen reduction technology (CryoLife Inc., Kennesaw, Ga.). Details and important considerations about these alternative graft compositions are described in Glickman, M. H., *J Vasc Surg* 34:45-472 (2001); Matsuura et al., *Ann Vasc Surg* 14:50-55 (2003); Bolton et al., *J Vasc Surg* 36:464-468 (2002); and Scher, L. A. and H. E. Katzman, *Sem Vasc Surg* 17(1):19-24 (March, 2004).

Recognized Vascular Graft Deficiencies, Defects, and Failures

Today, the range of materials used for making vascular graft implants include many different substrates, such as tanned natural vessels, textiles made from woven or knitted polyethylene terephthalate (DACRON), and extruded tubes made from expanded polytetrafluoroethylene (PTFE). Graft articles made using these materials have proven to be successful for large diameter artery replacement where there is a high blood flow rate; but unfortunately they have a much lower success rate in blood vessels with an inner diameter size less than 6 mm. In addition, the substrates comprising these conventionally used vascular grafts do not permit unrestricted ingrowth from the surrounding tissue after in-vivo implantation, owing mostly to the existence of ingrowth spaces within the substrate material that are either too narrow or are discontinuous. Equally important, all of the presently used graft substrates and constructions eventually fail in-vivo—either because of occlusion due to thrombosis (fibrous tissue build up), or because of intimal hyperplasia (exuberant muscle growth at the interface between artery and graft).

In addition, various factors—such as the thrombogenic nature of the graft material, the severity of surface roughness, the mechanical and/or haemodynamic properties of the graft, and the condition of the host blood vessel—are all known to influence the success of the implanted graft in-vivo. Although the reasons for failure are not fully understood, it is largely agreed that compliance mismatch between blood vessel and graft is the predominant issue surrounding the failure of small diameter prostheses. Discontinuity in mechanical properties between the graft and artery alters the blood flow resulting in a fibrous tissue build-up leading to the complete occlusion and hence failure of the graft.

Accordingly, autologous graft blood vessels, such as the saphenous vein and the internal mammary artery are still considered today to the best grafts for the reconstruction of small peripheral arteries, but these are often too diseased or unsuitable in the host for use as a graft. It is unfortunate also that none of the presently available synthetic textile grafts (PTFE and DACRON) have proved successful for long periods of time in-vivo. Many approaches to graft production have been developed in an effort to create a porous polyurethane artery graft. Indeed, it has been shown that it is possible to create an initially compliant porous graft; however, the long-term success for such grafts is unknown and unreliable. It is thus apparent that the material substrates currently used for graft construction are ineffectual and that an entirely new approach is necessary.

The Current Situation

It is clearly evident that the presently available small diameter grafts do not provide an acceptable long-term patency. It is now apparent that none of the previous known vascular prostheses have a structure similar to a naturally occurring blood vessel, or behave mechanically as a natural artery or vein does in the living subject. Thus, despite the many recent medical advances in the prosthetic vascular graft field occurring to date, there is no small-diameter (less 6 mm internal diameter) vascular prosthesis clinically available today that is capable of emulating the biological and physical properties of the normal blood vessel wall.

The presently existing prosthetic grafts made from current biomaterials that are implanted within the vascular system continue to fail primarily because of acute thrombosis. This recurring failure is attributed to the lack of endothelial cells at the biomaterial/blood interface that a native blood vessel possesses. Additionally, the current "gold standard" materials employed for large/medium-size diameter prosthetic grafts are relatively stiff compared to the flexibility of a native artery that has circumferential compliance. Thus, development of an "off-the-shelf" small vessel prosthesis which emulates some of the natural biologic processes of normal arterial walls would greatly expand the surgical options in treating both peripheral vascular disease as well as coronary artery disease.

SUMMARY OF THE INVENTION

The present invention is a major advance in the development of biomedical materials, devices and constructs. Accordingly, the invention has multiple aspects, some of which may be defined as follows.

A first aspect provides a fabricated textile conduit useful as a tangible workpiece for the manufacture of a prosthetic vascular graft construct, said fabricated textile article comprising:

a nanofibrous biocomposite material comprised of at least one biodurable synthetic substance and at least one extracellular matrix protein and fabricated as an elongated, hollow tube via an electrospinning perfusion process, said fabricated textile conduit having determinable inner wall and outer wall diameter sizes, two open ends, and an internal lumen less than about 6 millimeters in diameter, and presenting a discrete interior wall surface and an exterior wall surface, and being biocompatible for the conveyance of blood through its internal lumen.

A second aspect of the present invention is a prosthetic vascular graft construct useful as a synthetic blood vessel in-vivo, said prosthetic vascular graft construct comprising:

a fabricated textile conduit comprised of a nanofibrous biocomposite material which is composed of at least one kind of biodurable synthetic substance and at least one kind of extracellular matrix protein and which has been fabricated as an elongated hollow tube via an electrospinning perfusion process, said fabricated textile conduit having determinable inner wall and outer wall diameter sizes, two open ends, and an internal lumen less than about 6 millimeters in diameter, and presenting a discrete interior wall surface and an exterior wall surface, and being biocompatible for the conveyance of blood through its internal lumen.

at least one bifunctional linking agent joined to said wall surfaces of said fabricated textile conduit;

at least one pre-chosen biologically active compound which is permanently bound by said bifunctional linking agent then joined to said wall surfaces of said fabricated textile conduit, said prechosen compound having recognized biologically active properties for mediating the conveyance of blood while being attached to said fabricated textile conduit.

A third aspect includes a method for making a fabricated textile conduit useful as an antecedent workpiece for the manufacture of a prosthetic vascular graft construct, said method comprising the steps of:

preparing a fluid admixture comprised of at least one biodurable synthetic substance, at least one kind of extracellular matrix protein, and an organic liquid carrier;

subjecting said prepared fluid admixture to an electrospinning perfusion process; and fabricating an elongated hollow textile conduit composed of a nanofibrous biocomposite material via said electrospinning perfusion process, whereby said fabricated textile conduit (i) has determinable inner wall and outer wall diameter sizes, two open ends, and an internal lumen less than about 6 millimeters in diameter, and (ii) presents a discrete interior wall surface and an exterior wall surface, and (iii) is biocompatible for the conveyance of blood.

A fourth aspect of the present invention provides a method for making a prosthetic vascular graft construct, said method comprising the steps of:

preparing a fluid admixture comprised of at least one biodurable synthetic substance, at least one extracellular matrix protein, and an organic liquid carrier;

subjecting said prepared fluid admixture to an electrospinning perfusion process; and fabricating an elongated hollow textile conduit composed of fibrous biocomposite material via said electrospinning perfusion process, whereby said fabricated textile conduit (i) has determinable inner wall and outer wall diameter sizes, two open ends, and an internal lumen less than about 6 millimeters in diameter, and (ii) presents a discrete interior wall surface and an exterior wall surface, and (iii) is biocompatible for the conveyance of blood through its internal lumen;

combining at least one bifunctional linking agent and at least one pre-chosen biologically active compound to generate an intermediate complex, said pre-chosen compound having recognized biologically active properties for mediating the conveyance of blood in-vivo;

reactively adding said intermediate complex to said fabricated textile conduit whereby said active compound of said intermediate complex becomes permanently bound to said wall surfaces of said fabricated textile conduit, and wherein said permanently bound compound retains its recognized biologically active properties for mediating the conveyance of blood in-vivo.

A fifth aspect of the instant invention provides an alternative method for making a nanofibrous prosthetic vascular graft construct, said alternative method comprising the steps of:

obtaining a fabricated textile conduit composed of nanofibrous biocomposite material which has been formed using an electrospinning perfusion process, whereby said fabricated textile conduit (i) is comprised of at least one biodurable synthetic substance and at least one kind of extracellular matrix protein fiber, (ii) has determinable inner and outer diameter dimensions, two open conduit ends, and an internal lumen less than about 6 millimeters in diameter, (iii) presents a discrete interior wall surface and an exterior wall surface, and (iv) is biocompatible for the conveyance of blood through its internal lumen;

combining at least one bifunctional linking agent and at least one pre-chosen biologically active compound to generate an intermediate complex, said pre-chosen compound having recognized biologically active properties for mediating the conveyance of blood in-vivo;

reactively adding said intermediate complex to said fabricated textile conduit whereby said active compound of said intermediate complex becomes permanently bound to said wall surfaces of said fabricated textile conduit, and wherein said permanently bound compound retains its recognized biologically active properties for mediating the conveyance of blood in-vivo.

A sixth aspect of the present invention is an electrospinning perfusion method for fabricating a textile conduit, said method comprising the steps of:

erecting an electrospinning perfusion assembly comprised of a rotating mandrel which can be set at a selected rotation speed, a perfusion instrument which can be set at a specified liquid flow rate, and an electrical coupling for controlling and coordinating the actions of said perfusion instrument upon said rotating mandrel;

preparing a fluid admixture comprised of at least one biodurable synthetic substance, at least one kind of extracellular matrix protein, and an organic liquid carrier;

introducing said prepared fluid admixture to said perfusion instrument of said assembly;

perfusing said fluid admixture onto said rotating mandrel for a predetermined time such that a textile conduit is fabricated, whereby said fabricated textile conduit (i) is an elongated hollow tube of determinable dimensions and comprised of nanofibrous biocomposite material, (ii) has determinable inner wall and outer wall diameter sizes, two open ends, and an internal lumen less than about 6 millimeters in diameter, (iii) presents a discrete interior wall surface and an exterior wall surface, and (iv) is biocompatible for the conveyance of blood.

BRIEF DESCRIPTION OF THE FIGURES

The present invention may be more easily understood and more readily appreciated when taken into conjunction with the accompanying drawing, in which.

DETAILED DESCRIPTION OF THE INVENTION

Figure 1:
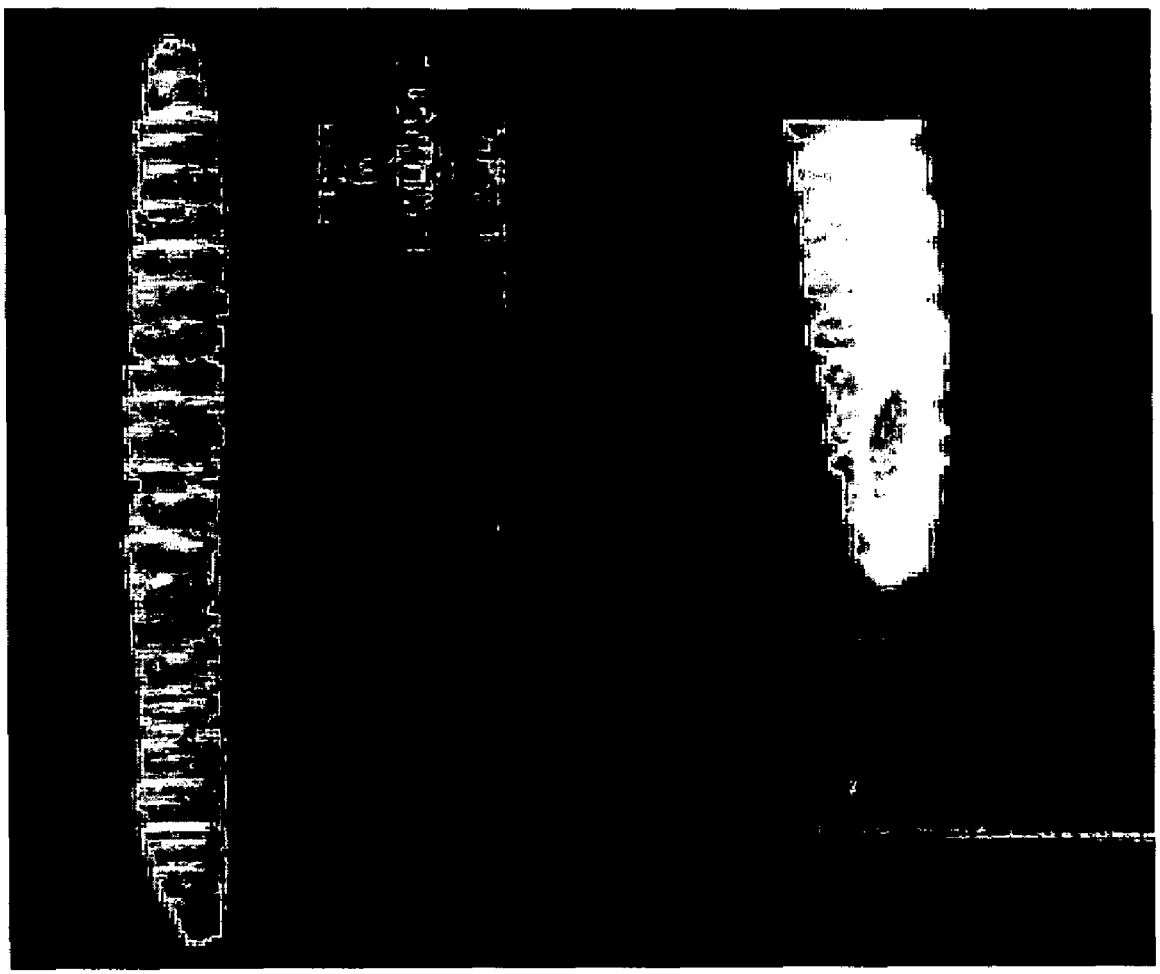
FIG. 1 is a perspective view of the exterior wall surface of a fabricated textile conduit.

I. The Subject Matter of the Present Invention as a Whole

The present invention comprises a bioactive, small-diameter (typically less than 6 mm in internal diameter) nanofibrous vascular graft prosthesis which is preferably manufactured using an unique electrospinning perfusion methodology. One preferred embodiment provides a nanofibrous biocomposite material which is formed as a discrete textile conduit from a prepared liquid admixture of DACRON polyester, a biodurable synthetic polymer; Type IV collagen, an extracellular matrix protein; and a liquid organic carrier. The prepared liquid admixture and fluid blending of diverse matter is employed in a novel electrospinning perfusion process to form a small-diameter (less than 6 mm inner channel) fabricated textile conduit, which in turn, serves as the antecedent precursor and tangible workpiece for subsequently making the prosthetic vascular graft construct.

In this manner therefore, after the biocomposite textile conduit has been fabricated as an elongated tubular article, one or more pre-chosen biologically-active molecules are then subsequently permanently bound (covalently or ionically) to the surfaces of the textile conduit wall. These permanently bound molecules are chemical compounds which retain their recognized biological activity after becoming permanently immobilized to the textile wall surface; and, via such immobilization, provides the textile conduit wall with many of the highly desired attributes and properties characteristic of naturally occurring blood vessels. Accordingly, after the immobilization of one or more biologically active molecules to the wall surfaces, the article is then most suitable for use in-vivo as a prosthetic vascular graft construct.

The availability of such small-diameter nanofibrous vascular graft prostheses with bioactive textile walls will have a significant impact on the vascular surgeon's ability to repair and/or replace small channel blood vessels in-vivo. These nanofibrous vascular graft materials can be utilized as bypass tubular grafts in peripheral blood vessel bypass procedures and/or as blood carrying conduit implants in coronary artery bypass procedures, of which there are presently over 500,000 operations performed annually in the United States alone.

The present electrospinning perfusion method of making prosthetic nanofibrous graft articles provides several major advantages and desirable benefits to the commercial manufacturer as well as to the vascular surgeon and medical practitioner. Among these are the following:

1. The manufacturing methodology comprising the present invention does not utilize any immersion techniques and does not require submerging the fabricated textile article in any immersion baths, soaking tanks, or dipping pools for any purpose. Rather, the methodology preferably utilizes the unique technique of electrospinning perfusion as a manufacturing method in order to blend a synthetic substance and an extracellular matrix protein together as a fabricated textile conduit having an unusually small inner diameter size.

2. The electrospinning perfusion method of manufacture yields a fabricated textile conduit having particular characteristics. The fabricated textile conduit is an elongated hollow tube having two discrete open tubular ends; is a tube having a predetermined inner diameter which typically is less than 6 mm in size; and is preferably a nanofibrous composite comprised of multiple fibers, with a determinable individual fiber thickness in or near the nanometer size range and a discernible fiber organization and distribution pattern.

3. The manufacturing method comprising the present invention also preferably employs limited heat and compression force to alter the exterior surface of the fabricated textile conduit wall originally formed via the electrospinning perfusion technique. This exterior surface treatment portion of the manufacturing process is optional, but produces a highly desirable crimped exterior surface for the tube over the entire length of the fabricated textile conduit. The inner diameter size (typically less than 1 mm to no larger than about 6 mm) of the crimped fabricated textile conduit nevertheless remains the same, despite the limited heating and compression treating of the tubular exterior surface.

4. The protein of choice which is to be permanently attached subsequently to the surface of the crimped fabricated textile conduit will retain its characteristic biological activity after being immobilized and bound to the textile graft wall material. The attributes and properties associated with the protein of choice will co-exist with and be an integrated feature of the resulting vascular graft article at the time it is utilized in-vivo as a prosthesis.

Wording, Terminology, and Titles

Although many of the words, terms and titles employed herein are commonly used and conventionally understood within its traditional medical usage and scientific context, a summary description and definition is presented below for some phrases and wording as well as for particular names, designations, epithets or appellations. These descriptions and definitions are provided as an aid and guide to recognizing and appreciating the true variety and range of applications intended for inclusion within the scope of the present methodology.

To perfuse and a perfusion: The action and the act of causing a liquid or other fluid to pass across the external surfaces of or to permeate through the substance of a tangible entity or configured physical construct. Perfusion of a liquid or fluid thus includes the alternative actions of: a sprinkling, pouring, or diffusing through or overlaying action; a covering, spreading, penetrating or saturating action (termed "suffusion"); a slow injection or other gradual introduction of fluid into a configured space or sized internal volume (termed "infusion"); and a passage across a surface or through a discrete surface or tangible thickness of matter, regardless of the mechanism or manner of transfer employed for such fluid passage.

To immerse and an immersion: The action and the act of dipping, plunging or sinking a discrete entity or tangible item completely such that it is entirely submerged within a quantity of liquid or a volume of fluid. Immersion of a discrete entity or tangible item includes the alternative actions of:

dunking, soaking, bathing, or flooding the entity within a liquid or fluid bath, tank, or pool; and the enveloping or burying of the tangible item in the liquid or fluid completely such that the item disappears from the surface and lies within the substance of the liquid or fluid matter.

Woven fabric: A cloth where discrete fibers are first combined into yarns, and the yarns are then interlaced together in some degree during a fabrication process to produce the resulting woven fabric. For purposes of the present invention, any fabric comprised of yarns is by definition is deemed to be a woven fabric, without regard to the particular manner of its combining of fibers into yarns; and is alternatively exemplified by interwoven, knitted, and interlaced yarns as woven fabric articles Non-woven fabric: A web of material produced directly from fibers without first making yarns. The web of fibers is produced by carding, air-layering or wet-laying; and is subsequently bonded or entangled by needle punching, waterjets ("spunlacing"), chemical glues, or by using chemical means. Those methods that combine web formation and bonding include melt blowing. The non-woven manufacturing process is typically used to yield light-weight, disposable fabrics and cloths.

Fabricated textile conduit: A hollow, tubular article of manufacture which is comprised, in whole or in part, of fibers arranged as a fabric; and without regard to whether the fabric is a woven or a non-woven article. The fibers comprising the fabricated textile conduit may be chosen from a diverse range of organic synthetics, prepared polymer compounds, or naturally-occurring matter. In general, the fabricated textile conduit is prepared as a cloth or fabric; and may comprise a single fiber film, or a single layer of fibrous matter, or exist as multiple and different deniers of fibers which are present in a range of varying thickness, dimensions, and configurations.

Aqueous mixture, liquid or fluid: By definition, any mixture, liquid or fluid which contains or comprises water in any meaningful quantity or degree. Although many other compositions, substances, or materials may exist within the mixture, fluid or liquid in a variety of physical states, the bulk or majority of volume for such fluids is water.

Organic liquid-miscible substance: By definition, any composition, compound, polymer material or matter in any physical state (i.e., gaseous, liquid or solid) that is capable of being mixed or combined with a liquid organic carrier. This term thus includes within its meaning a variety of alternative conditions and physical states for any substance which is capable of: (i) being soluble in any meaningful degree in a liquid organic solvent or an organic solvent blending; (ii) being dissolved or solubilized in any measurable quantity in an organic liquid or an organic fluid blending (whether or not a solution is formed); (iii) being able to be dispersed, suspended, or carried in any quantity in an organic liquid or an organic fluid blending (whether or not a homogeneous suspension is formed); (iv) being able to be mixed or combined while in a simple, linear, branched, or polymerized condition or while existing in an aggregate, complex, clustered or confluent state; (v) becoming ionized or ionisable in an organic liquid or an organic fluid mixture; and (vi) being able to be distributed in any degree in an organic liquid or an organic fluid mixture while in a non-ionized state or condition.

II. The Fabricated Textile Conduit and its Role as an Antecedent Precursor in the Making of a Prosthetic Vascular Graft Construct The method of the present invention is directed in part to the making of a fabricated textile conduit, an antecedent article of manufacture, which is then employed as a workpiece by the remaining steps of the method to generate the prosthetic vascular graft construct. This term "fabricated textile conduit" has been defined in meaning and described in scope above; and applies generally to any article, device, appliance, or construct which contains fibers, or is constituted of fibrous matter, or has as a component part—in whole or in part—a fabric, cloth, or material substance comprised of discrete fibers. The broad scope of this term is intentional; and is deemed to cover and apply to any and all textile containing biomedical devices, items, entities, apparatus, appliances, and instruments which are biocompatible with and/or can be surgically implantable into the vascular system of a living subject, human or animal.

Once the fabricated textile conduit has been manufactured and exists as a discrete entity, it serves as a tangible article and workpiece for subsequent chemical reaction to yield the desired end product, termed a "prosthetic vascular graft construct". Thus, regardless of its true chemical composition/ formulation or the particular mode of construction, the initially formed 'fabricated textile conduit' and the subsequently generated 'prosthetic vascular graft construct' are directly and intimately related; and thus share a number of specific qualities and characteristics in common. These shared attributes include:

(i) Each article is an elongated hollow tube having a determinable overall tubular length and two open ends;

(ii) Each article is a non-perforated, solid wall tube of round or oval cross-sectional configuration which has a determinable girth and a fixed outer and inner diameter size; and (iii) Each article is a tube which has at least one internal lumen of determinable volume which is co-incidental and coextensive with the internal wall surface and has at least one exterior wall surface which is co-incidental and co-extensive with the outer wall topography.

The Chemical Composition of the Fabricated Textile Conduit

By definitional requirement, the fabricated textile conduit (the antecedent forerunner of each prosthetic vascular graft construct) is a woven article comprised of discrete fibers or threads. The chemical composition of the fibrous composite material forming the fabricated textile conduit is an admixture and blending of at least two different materials: a naturally-occurring extracellular matrix protein; and a synthetic substance. This admixture of two diverse chemical compositions is combined together in a wide range of varying ratios using a liquid carrier, followed by application of an electric current to create nanofibers.

To illustrate the range and variety of synthetic substances deemed suitable for combination as a blended mixture, the listings of Tables 1 and 2 are presented below. It will be noted that the listing of Table 1 presents the naturally occurring extracellular matrix proteins which are known today to exist in nature. In comparison, the listing of Table 2 provides some representative synthetic substances compositions long deemed suitable for use as synthetic fibers. In addition, Table 3 lists some of the more commonly available organic liquids and fluids which can be typically employed as liquid carriers for the fibrous admixture.

TABLE 1

Some Naturally-Occurring Extracellular Matrix Proteins
Fibrous Proteins

Elastin;
Collagen, Types I, II, III, IV, and V respectively;
Fibrinogen;
Fibrin;
and any mixture of these.

TABLE 2

Illustrative Synthetic Substances

Polymeric Fibers polyethylene terephthalate;
nylon;
polyurethane;
polyglycolic acid;
polyamides;
polytetrafluoroethylene;
polyesters;
and mixtures of these substances.
Other synthetic fiber compositions acetate;
triacetate;
acrylics, such as acrylonitrile;
aramid;
olefins, such as polypropylene and polyethylene
saran.

TABLE 3

Representative Organic Liquid Carriers

Organic Liquid Carriers

Hexafluoroisopropanol;
Dimethylformamide;
Dimethylsulfoxide;
Acetonitrile;
Acetone;
Hexamethylphosphoric triamide;
N,N-diethylacetamine;
N-methylpyrrolidinone;
Ethanol.

Inorganic Liquid Carriers

NMMO (n-methylmorpholine oxide);
Water.

At least some of the fibers comprising the fabricated textile conduit of the prosthetic graft will demonstrate a range of properties and characteristics, as follows.

1. The fibers constituting the fabricated textile conduit (and the subsequently generated prosthetic vascular graft construct) will have a demonstrable capacity to take up water and/or aqueous liquids and fluids (with or without direct wetting of the fiber material). The mode or mechanism of action by which water and aqueous fluids is taken up by the fibers of the textile (and/or become wetted by the aqueous fluid) is technically insignificant and functionally meaningless. Thus, among the different possibilities of water uptake are the alternatives of: absorption; adsorption; cohesion; adhesion; covalent bonding; non-covalent bonding; hydrogen bonding; miscible envelopment; water molecule entrapment; solution-uptake between fibers; fiber wetting; as well as others well documented in the scientific literature. Any and/or all of these may contribute to water or aqueous fluid uptake in whole or in part. Which mechanism of action among these is actively in effect in any instance or embodiment is irrelevant.

2. By choosing the particular chemical formulation and/or stereoscopic structure for the material substance of the fabricated conduit, the resulting textile can be prepared as a structured article having a markedly long duration and lifespan for functional in-vivo use. Thus, by choosing one or more durable and highly resilient chemical compositions as the fibers of choice, fabricated textile conduits effective for many years' duration and medical utility may be routinely made. All of these choices and alternatives are conventionally known and commonly used today by practitioners in this field.

3. The fibers comprising the fabricated textile conduit (and the subsequently generated prosthetic graft construct) can be utilized in a variety of organizations as a tangible structure. Thus, as conventionally recognized within the textile industry, the fabricated textile conduit may vary in denier size or thickness; and may optionally receive one or more interior and/or exterior surface treatments to enhance particular attributes such as increased in-vivo biocompatibility or a greater expected time for functional operation and use in-vivo. All of these organizational variances are routine matters which will be optionally chosen and used as a matter of particular needs or personal choices.

4. The fibers comprising the fabricated textile conduit (and the subsequently generated prosthetic vascular graft construct) can be prepared to meet the particular intended use circumstances or contingencies of the particular application. Thus, the formed textile fabric can alternatively be prepared either as a relatively thin-walled conduit or as a thick-walled configured tube; be produced as an elongated conduit in a diverse range of different outer diameter and inner diameter sizes; and be fashioned as a relatively inflexible or unyielding conduit or as a very flexible and easily contorted length of hollow tubing.

III. The Unique Electrospinning Perfusion Method

A. The Steps Comprising the Electrospinning Perfusion Technique

The preferred method for making the fabricated textile conduits of the present invention is via the unique technique of electrospinning perfusion. For this purpose, an electrospinning perfusion assembly is erected which comprises, at a minimum, a rotating mandrel which can be set at a pre-selected rotation speed; a needle fronted perfusion instrument which can be set to deliver a liquid mixture at a pre-specified flow rate; an electrical coupling for controlling and coordinating the electrical voltage applied across the perfusion needle and which is grounded to the rotating mandrel; and a controllable supply of electrical power.

Utilization of this assembly permits uniform coating of the liquid mixture onto the surface of the mandrel; and the applied electrical voltage can be varied as needed to control the formation of the nanofibers upon the mandrel's surface.

Also for use in this erected assembly, a prepared mixture of extracellular matrix protein and synthetic material is blended together into an organic liquid carrier. For example, a preferred liquid mixture is obtained by the blending of 19% w:v polyethylene terephthalate (DACRON) and 1.4% w:v Type IV collagen in a sufficient quantity of ice-cold hexafluoroisopropanol.

For fabricating small batches of product using this unique method, a chemically resistant syringe with a stainless steel blunt spinneret can serve as a functional instrument for perfusion. Alternatively, of course, any other tool, assembly or instrument capable of performing perfusion at a pre-selected flow rate and reaction temperature can be usefully employed.

In this small batch system, the perfusion syringe of the assembly is filled with the prepared liquid mixture described above and placed onto a Harvard Apparatus syringe pump. The perfusion rate is preferably set at 3 ml/hour at 25° C. If desired, however, the flow rate can be increased and/or decreased to meet specific requirements.

A PTFE-coated stainless steel mandrel (diameter=4 mm) was set at a jet gap distance of 15 cm from the tip of the syringe needle. Gap distance can be varied at will to change the fiber diameter size. The rotable mandrel was then electrically grounded to the power source, with the positive high potential source connected to the syringe needle. The mandrel rotates or spins at a pre-selected rate of rotation throughout the act of liquid perfusion.

Perfusion of the polymer solution begins upon application of the electric current to the tip of the syringe needle (typically 15 kV), which then moves at a preset constant speed and fixed distance from the mandrel surface for a limited time period (typically about 40-60 minutes in duration). This process of manufacture is therefore termed "electrospinning perfusion"; and yields a fully fabricated, elongated nanofibrous textile conduit whose inner diameter size corresponds to the overall diameter of the mandrel (in this instance, 4 mm).

After being formed as a hollow tube by electrospinning perfusion, the thickness and girth of the originally formed fibrous composite wall and exterior surface preferably is then intentionally altered into a crimped structural form via a limited heat set technique, followed by compression of the fibrous composite wall, in order to provide kink-resistance for the elongated tube.

In brief, the end portions of the formed hollow tube (appearing about 1 cm from each end of the mandrel) were cut off and discarded. The remainder of the elongated hollow tube was then stretched 25% of the starting segment size while on the mandrel in order to provide a set strain across the fibers, a manipulation that occurs in normal fiber extrusion. The stretched tubes were then immediately exposed to 100% ethanol for 2 hours time at room temperature in order to remove the residual solvent. The created kink-resistance effect and overall result is shown by FIG. 1.

B. The Tangible Textile Conduit Fabricated by this Method

The fabricated textile conduit has a number of unique structural features which are the direct result and characteristic of its novel mode and manner of manufacture.

1. The textile conduit fabricated via the electrospinning perfusion technique yields a discrete tubular article of fixed inner-wall and outer wall diameters, and a solid wall girth and configuration formed of a nanofibrous composite composition. The material substance of the fabricated conduit wall typically includes at least two differently sized fibers: The extracellular matrix protein is present primarily as discrete nanometer or $10^{-9}$ meter sized fibers throughout the composite, while the synthetic substance is present as fibers which are about ten times larger in thickness—that is, as discrete fibers about $10^{-8}$ meters in diameter size. These fiber size differences are clearly demonstrated by the empirical data presented below and is visibly evident via FIG. 2.

2. The interior wall surface and the exterior wall surface of the preferred fabricated textile conduit are markedly different. Owing to the crimping and heat setting treatments following the initial electrospinning perfusion steps of the methodology, the exterior wall surface has a crimped and somewhat irregular appearance. In comparison, the interior wall surface and the internal lumen of the conduit as a whole presents a smooth, regular, and even appearance which is devoid of perceptible projections, lumps, indentations, and roughness.

3. The material substance of the nanofibrous composite tubular wall is resilient and can be prepared in advance to provide varying degrees of flexibility, springiness, suppleness, and elasticity. Moreover, the nanofibrous composite wall is durable and strong; is hard to tear, cut, or breakup; and is hard-wearing and serviceable for many years' duration.

4. The fibrous material substance of the fabricated textile conduit is biocompatible with the cells, tissues and organs of a living subject; and can be implanted surgically in-vivo without initiating or inducing a major immune response by the living host recipient. While aseptic surgical technique and proper care against casual infection during and after surgery must be exercised, the fabricated textile conduit can be usefully employed as a vascular substitute and effective replacement for a clogged or damaged blood vessel in-vivo.

C. The Major Benefits and Advantages of the Electrospinning Perfusion Technique The electrospinning perfusion technique has a number of advantages over previously known manufacturing processes. One of the primary benefits is that no exogenous binder agents are required by the process either to form the substance of or to maintain the integrity of the fabricated textile conduit. Also, both the synthetic substance and the extracellular matrix protein can be generated into fiber form owing to the lower temperatures used by the electrospinning perfusion process. In addition, the nanofibers within the conduit wall act to seal the interstices of the graft; therefore no sealants as such are required. This manufacturing technique also benefits the manufacturer in that the technology is not a dipping or immersion method of preparation, which typically requires the addition of extreme heat.

Furthermore, the electrospinning perfusion technique yields a fabricated textile conduit as a graft material in which both kinds of fibers (Dacron and Collagen) co-exist independently and are visibly evident throughout the fabricated textile. This structural distribution of two different types o fibers within the fabricated textile adds strength and flexibility to the graft material as a whole Also, the presence of collagen fibers provides anchor sites to which diverse biological proteins (such as growth factors, anti-coagulants, antimicrobials, antineoplastic agents, and the like) can be attached

IV. The Permanently Bound Biologically Active Compound

A. The Choosing of a Mediating Chemical Compound

A number of different biologically active chemical compounds—including proteins and proteinaceous matter, saccharides, and polysaccharides, and oligonucleotides—can be beneficially and advantageously utilized in tandem with the fabricated textile conduit when constructing and chemically preparing the surface of the fibrous matter as a prosthetic vascular graft. However, there are several minimal requirements and qualifications which the biologically active molecule—whatever its particular composition and formulation as a chemical compound—must demonstrably provide in order to be suitable for use in the present invention. These are:

(i) The chosen compound or molecule must be capable of demonstrating its characteristic biological activity before being covalently or ionically bound to the wall surface of the fabricated textile conduit. This characteristic biological activity constitutes its ability/capacity to function as a mediator in-situ for the conveyance of blood in-vivo.

(ii) The particular compound or molecule immobilized on the wall surface of the fabricated textile conduit must be capable of demonstrating its characteristic biological activity (its mediating capacity) after being covalently or ionically bound; and (iii) The compound or molecule covalently or ionically bound to the wall surface of the fabricated textile conduit must retain its characteristic biological activity (its mediating capacity) over an extended period of time after the conduit has been utilized in-vivo.

In addition, since the primary application of the graft conduit is to be a vascular graft prosthetic material, it is preferred that the characteristic biological properties of the chosen compound (be it a protein or proteinaceous matter, a saccharide or polysaccharide, or an oligonucleotide) serve as adjuncts to and promoters of the natural processes occurring in-vivo for the repair blood vessels and/or the reconstruction of vascular tissues. Accordingly, it is deemed desirable that the primary function and capabilities of the chosen biologically active molecule not be antimicrobial as such; but rather act selectively as a physiological aid and/or pharmacological agent—i.e., as a mediator which serves to avoid blood coagulation, and/or acts to prevent the formation of blood clots, and/or function as an entity which deactivates specific types of cells, and/or functions to suppress or inhibit a variety of different humoral and cellular responses associated with or related to inflammation and the inflammatory response in-vivo.

Some exemplary biologically active chemical compounds which are blood flow mediators and can be immobilized and permanently bound to the surface of the fabricated textile article are listed by Tables 4 and 5 below:

TABLE 4

Representative Biologically Active Proteins and Proteinaceous Matter

Growth Factors

Platelet derived growth factor (PDGF);
Epidermal growth factor (EGF), also known as vascular endothelial growth factor (VEGF);
Macrophage derived growth factor (MDGF);
Fibroblast growth factor (FGF); and
Nerve growth factor (NGF).
Blood Anti-Coagulation Proteins Antibodies or peptide fractions specific for any of blood Factors I-XII respectively;
Antibodies or peptide fractions specific against Vitamin K;
Hirudin; and
Albumin.
Selected cytokines (enzymes)

Interleukin-1 (IL-1), an endogenous pyrogen and major inflammatory mediator;
Interleukin-2 (IL-2), a T-cell activator and growth factor;
Interleukin-3 (IL-3), a hematopoietic growth factor;
Interleukin-4 (IL-4), a T-cell and B-cell growth factor;
Interleukin-5 (IL-5), a promoter of eosinophil growth and differentiation and IgA antibody synthesis;
Interleukin-6 (IL-6), a B-cell differentiation factor;
Interleukin-7 (IL-7), a growth factor for early B- and T-lymphocytes;
Interleukin-8 (IL-8), a chemotactic factor for neutrophils and lymphocytes;
Interleukin-10 (IL-10), a down-regulator of cell activation;

TABLE 4-continued

Representative Biologically Active Proteins and Proteinaceous Matter

Interleukin-12 (IL-12), an augmenter of IFN-γ production;
Interleukin-13 (IL-13), a factor which overlaps in function with IL-4;
Tumor necrotic factor (TNF), a factor which overlaps in function with IL-1 and mediates host response to gram-negative bacteria;
Interferons-α, -β, -γ, which activate macrophages, enhance lymphocyte and natural killer cells, and have antiviral and antitumor activity; and
Granulocyte-macrophage colony stimulating factor (GM-CSF), a growth factor for granulocytes, macrophages, and eosinophils
Lectins (mitogenic agents from plants)

Concanavalin A, a protein from the jack bean;
UEA I.
Glycoproteins and proteoglycans Ovalalbumin;
Avidin.

TABLE 5

Other Biologically Active Chemical Compounds

Oligonucleotides

RGD (and proteins/peptides containing sequence);
VCAM;
ICAM;
PCAM.
Saccharides and polysaccharides Glucosamine;
Chondroitin and chondroitin 4-sulfate;
Hyaluronic acid;
Heparin.

B. Permanently Immobilizing the Mediating Compound of Choice

The mediating compound of choice is to become covalently or ionically bound to the wall surface of the fabricated textile conduit. Afterwards, when the mediating molecule has become permanently immobilized and an integral part of the nanofibrous composite, the manufacturing process will be complete; and a ready to use prosthetic vascular graft construct will be the result.

The Bifunctional Linking Agents

The preferring mode of attachment for the mediating molecule of choice is via the use of at least one bifunctional linking agent. Such bifunctional linking agents are well recognized and conventionally known as a class of chemical compositions which function as cross-linking binders; and are routinely employed (singly or in multiples) to join one molecule to another.

Accordingly, some preferred bifunctional linking molecules or agents suitable for use in the instant methodology include, but are not limited to: sulfosuccinimidyl 4-(N-maleimidomethyl)cyclohexane-1-carboxylate (sulfo-SMCC); succinimidyl 4-(N-maleimidomethyl)cyclohexane-1-carboxylate (SMCC); Nsuccinimidyl-3-(2-pyridyldithio)propionate (SPDP); sulfosuccinimidyl 2-(7-azido-4-methylcoumarin-3-acetamide)ethyl-1,3'-dithiopropionate (SAED); 1-ethyl-3-(dimethylaminopropyl)-carbodiimide HCl (EDC); and Traut's reagent (2-iminothiolane hydrochloride).

In addition, many other diverse choices of bifunctional linking molecules or agents can also be usefully employed in this methodology and include, but are not limited to: ABH;

ANB-NOS; APDP; APG; ASIB; ASBA; BASED; BS$^3$; BMH; BSOCOES; DFDNB; DMA; DMP; DMS; DPDPB; DSG; DSP; DSS; DST; DTBP; DTSSP; EDC; EGS; GMGS; HSAB; LC-SPDP; MBS; M$_2$C$_2$H; MPBM; NHS-ASA; PDPH; PNP-DTP; SADP; SAED; SAND; SANPAH; SASD; SDBP; SIAB; SMCC; SMBP; SMPT; SPDP; Sulfo-BSO-COES; Sulfo-DST; Sulfo-EGS; Sulfo-GMBS; Sulfo-HSAB; Sulfo-LC-SPDP; Sulfo-MBS; Sulfo-NHS-ASA; Sulfo-NHS-LC-ASA; Sulfo-SADP; Sulfo-SAMCA; Sulfo-SANPAH; Sulfo-SAPB; Sulfo-SIAB; Sulfo-SMCC; Sulfo-SMBP; and Sulfo-LC-SMPT.

The specific choices of use concentration ranges, order of reactants, reactions times and conditions, and the like are conventionally known variable; and are thus left to the personal needs or preferences of the user.

The Expected Order of Binding Reactions

It is typically expected that when the biologically active compound of choice and the bifunctional linking agent are reactively combined together, an identifiable intermediate entity or coupled molecule will be generated as a consequence. The intermediate composition is in fact a complex form of the bifunctional linking agent joining with the protein of choice as a single entity. However, because a bifunctional linking agent is employed as the reactive moiety for further chemical reaction, the generated intermediate complex retains at least one unbound and functional reactive group for subsequent chemical reaction; and thus, the intermediate composition can subsequently be permanently joined to the wall surface of the previously prepared fabricated textile conduit.

Accordingly, as the empirical evidence presented hereinafter by the illustrative example clearly shows, when VEGF (one of the exemplary biologically active molecules) and Sulfo-SMCC (the 1$^{st}$ bifunctional linking agent) are reactively combined together, a VEGF-SMCC intermediate complex is generated as the result.

Then, when the generated VEGF-SMCC intermediate complex subsequently is reactively added to an admixture of fabricated textile conduit incubated in Traut's reagent (the 2$^{nd}$ bifunctional linking agent), a second binding reaction occurs; and a permanent immobilization and binding of the VEGF to the wall surface of the fabricated textile conduit is the result. In this manner, via the use of multiple bifunctional linking agents to immobilize the protein of choice, a prosthetic vascular graft construct having an immobilized biologically active molecule on the wall surface is obtained.

V. Experiments, Empirical Data, and Results

To demonstrate the merits and value of the present invention, a series of planned experiments and empirical data are presented below. It will be expressly understood, however, that the experiments described herein and the results provided below are merely the best evidence of the subject matter as a whole which is the present invention; and that the empirical data, while limited in content, is only illustrative of the scope of the present invention as envisioned and claimed.

An illustrative recitation and representative example of the present invention is the preferred manner and mode for practicing the methodology is also presented below as part of the experimental method. It will be expressly understood, however, that the recited steps and manipulations presented below are subject to major variances and marked changes in the procedural details; all of which are deemed to be routine and conventional in this field and may be altered at will to accommodate the needs or conveniences of the practitioner.

Experimental Series A: Preparation and Characterization of ESDC Grafts

1. The Electrospinning Perfusion Technique

The Apparatus

For small batch purposes, a self-contained semi-automated electrospinning perfusion apparatus was assembled which included a Glassman power supply, a Harvard Apparatus syringe pump, an elevated holding rack, a modified polyethylene chamber, a pray head with power attachment, a reciprocating system, and a Wheaton stirrer for controlled mandrel rotation. Utilization of this assembly permits uniform coating of a liquid polymer onto the PTFE-coated stainless steel mandrel (diameter 4 mm). A 10 ml chemical-resistant syringe was filled with the liquid polymer; and a stainless steel 180 guage blunt spinneret (0.5 mm internal diameter) was cut in half, with the syringe fitting half connected to the chemical-resistant syringe.

Nalgene PVC tubing (1/32 ID×3/32 OD; 66 cm length) was then connected to the syringe, followed by connection to the other half of the blunt spinneret within the spray head. The line was purged of air, with the syringe then placed onto the syringe pump. The high potential source was connected to the spray head tip; and the mandrel was set at a jet gap distance of 15 cm from the tip of the needle. The mandrel was then grounded to the power source; and the perfusion rate was set at 3 ml/hour at 25° C.

The Liquid Polymer Blend

A composite Dacron (19% w:v)/Type IV collagen (1.5% w:v) polymer blend was prepared in ice-cold 100% hexafluoroisopropanol. The 10 ml syringe with a stainless steel 18-gauge blunt spinneret (0.5 mm internal diameter) was filled with the liquid polymer and placed onto the Harvard Apparatus syringe pump.

Perfusion of the polymer was then started upon application of the current to the tip of the needle (15 kV) with electrospinning proceeding for 40 minutes. After electrospinning, the end portions of the graft material (1 cm from each end of the mandrel) were cut off and discarded. The graft material was then stretched 25% of the starting segment size wile on the mandrel in order to provide a set stain acros the fibers, a process that occurs in normal fiber extrusion. The fibrous grafts were immediately exposed to 100% ethanol for 2 hours at room temperature in order to remove the residual solvent. For those segments in which kink-resistance was created, this ethanol treatment step was delayed until kink-resistance had been established.

Results

The fabricated DACRON and ESDC (i.e., ElectoSpun DACRON-Collagen) tubular grafts had a consistent 4 mm internal diameter throughout the lumen of their structures (length=7.5 cm). The wall of the ESDC tube had excellent flexibility after electrospinning for 40 minutes. However, this flexibility led to wall kinking at bend angles greater than 15 degrees. This demonstrated the need for creating kink-resistance properties within the fibrous wall of the graft tube.

Increasing electrospinning time significantly increased the rigidity of the biocomposite wall material (data not shown). Conversely, electrospinning for shorter periods of time (1-15 minutes) yielded a tubular structure without significant wall strength. Thus, 40 minutes of electrospinning time with this liquid polymer blending, applied voltage (15 kV0, and gap distance was employed for the formation of ESDC tubular grafts. The next step was to create kink-resistance for the tubular wall.

2. Establishment Of Kink-Resistance Within The Tubular Wall

Creating Kink-Resistance

After formation of the ESDC tube and prior to ethanol washing, kin-resistance was crated within the biocomposite tubular wall using a novel low temperature heat setting with compression of the wall. In a manner similar to ESDC tube formation, the end portions of the fibrous graft (1 cm from each end of the mandrel) were cut off after electrospinning and discarded. The remaining graft tube was ten stretched 25% of the starting segment size while on the mandrel to provide a set strain across the fibers. A U-shaped stainless steel wire (1 mm diameter) attached to a holding device was heated and placed gently against the ESDC tube while slowly turning the mandrel 180 degrees. This process then proceeded every 2 mm down the entire length of the graft tube.

After completion of the ring setting process, the ESDC graft tube was compressed on the mandrel and immediately placed in 100% ethanol for 2 hours at room temperature in the compressed state to remove the residual solvent. After this incubation period, the ESDC graft tube was stretched back to its normal length on the mandrel; removed from the mandrel; and then air dried overnight at room temperature. The overall result is shown by FIG. 1.

3. Evaluation of ESDC Grafts via Scanning Electron Microscopy

Several ESDC grafts prepared as described above were randomly selected and examined via a JEOL JSM 5900LV electron microscope in order to determine fiber size and distribution throughout the graft wall. A total of 20 (7 nanofibrous DACRON and 13 ESDC tubular grafts) were synthesized; and these grafts were employed for all the in vitro and in vivo studies.

Figure 2:
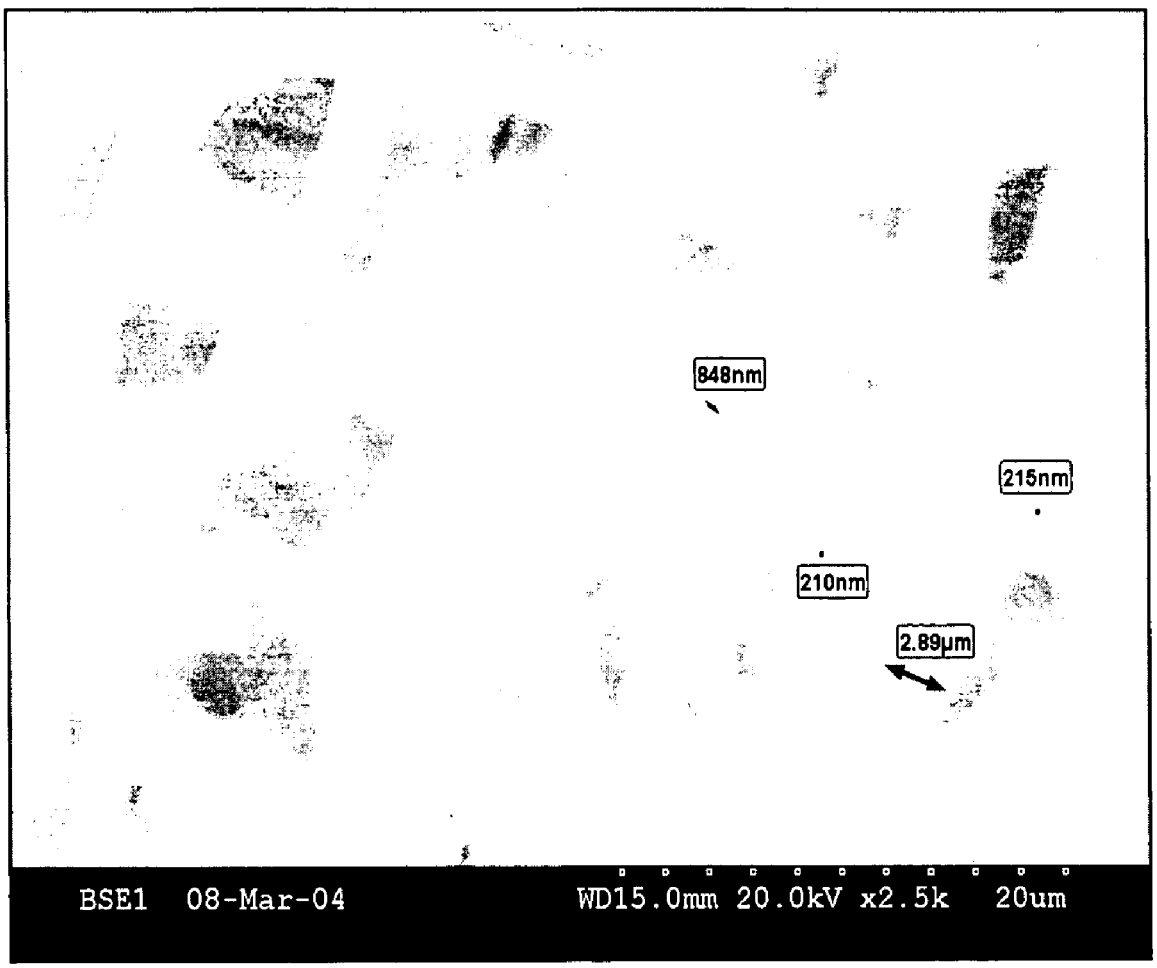
FIG. 2 is a visual image of the biocomposite nanofibrous material (ESDC) of the fabricated textile conduit of FIG. 1 which shows the relative thickness of its constituent fibers.

Analysis of these grafts via SEM showed that ESDC graft synthesis was very consistent owing to the semi-automated electrospinning perfusion apparatus as well as the controlled environmental conditions. SEM analysis revealed that two independent fibers were evident within the tubular biocomposite wall, as shown by FIG. 2. The fiber diameter sizes ranged from 100 nM to 300 nM. The smaller diameter fibers were shown to be collagen fibers, with the larger diameter fibers (ranging from 500 nM to 3000 nM) being the DACRON fiber. In comparison, the smaller nanofibers were not present when DACRON was electrospun alone (data not shown), thereby confirming the formation and presence of the collagen fibers within the ESDC graft wall.

4. Water Permeation Assessment for ESDC Grafts

Water Permeation

Water permeation assessments for the ESDC grafts prepared as described above was measured using previously published procedures [see Phaneuf et al., *Biomaterials* 22:463-468 (2001)]. In brief, all the ESDC grafts were opened in the longitudinal direction and then cut into circular segments (15 mm diameter, n=4 segments/test group). A cylindrical reservoir, with a direct water inlet to keep pressure constant, was set to a height of 165 mm to the top of the water column. A 5/16" Tight Right fitting (attached to 3/16" tubing) was used to hold control or test segments (area=0.38 cm$^2$) in place without applying stretch to the material.

Each circular ESDC graft piece was pre-soaked in the apparatus reservoir for 1 minute in order to de-gas the material, followed by exposure to 120 mm Hg pressure. Volume was collected in a graduated cylinder for 60 seconds (30 seconds for knitted DACRON due to open porosity) and used to determine ml/min/cm$^2$.

Figure 3:
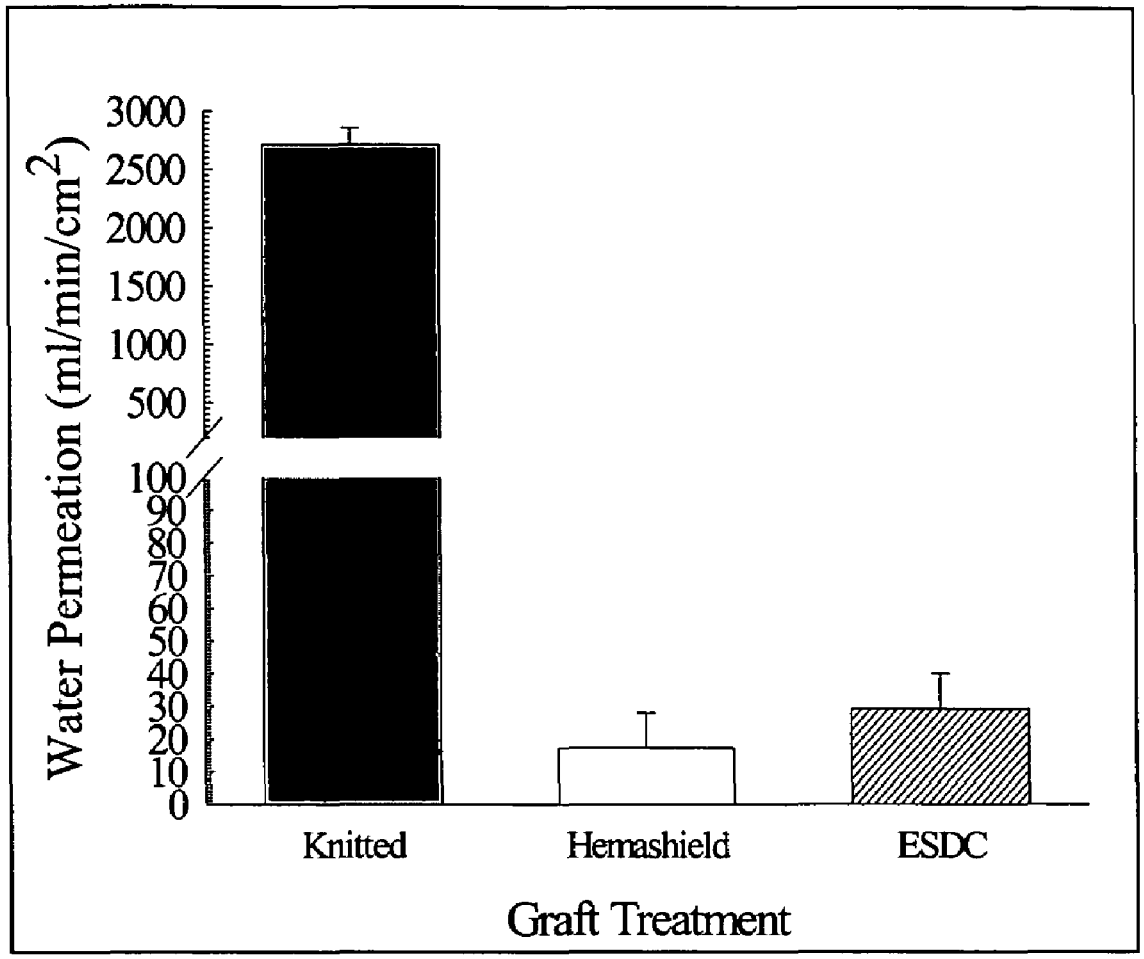
FIG. 3 is a graph presenting empirical data that walls of the prosthetic vascular graft construct are water permeable and prevent blood seepage.

Results:

Unmodified knitted Dacron grafts had a water permeation rate of 2,717±140 ml/min/cm$^2$, as shown by the graph of FIG. 3. Upon sealing of the knitted graft matrices with crosslinked collagen, the methodology performed for the Hemashield® graft, water permeation (17±11 ml/min/cm$^2$) was significantly decreased. Water permeation for the ESDC grafts was 29±11 ml/min/cm$^2$, comparable to the clinically used Hemashield® grafts (p=0.15). This water permeation result is significantly below the 100 ml/min/cm$^2$ threshold determined to prevent blood seepage through the graft wall. Thus, the ESDC graft was further evaluated for additional physical properties as well as chemical characterization.

5. Tensile Strength/Ultimate Elongation:

Tensile strength (pounds force), strain at maximum load (%) and strain at break (%) were measured using our published techniques. ESDC graft segments (7 mm width, 3 cm length; n=3/test condition) were measured and cut. A Q-Test Tensile Strength Apparatus (MTS Systems, Cary, N.C.) was calibrated according to manufacturer's specifications in a climate-controlled environment (room temperature=67° F, 45% relative humidity). The samples were also conditioned in this environment for 24 hours. Segment stretching (crosshead speed=50 mm/min, gauge length=2 cm, load cell=25 lb) was then initiated and terminated upon segment breakage.

Figure 4:
FIG. 4 is a set of visual images showing the ESDC grafts and nanofibrous DACRON grafts.

Results:

There was a marked difference between the nanofibrous Dacron and ESDC grafts in that there was presence of yield point and plastic flow for the ESDC grafts, which was notably absent in the nanofibrous Dacron grafts. See FIG. 4 and Table E1 below.

TABLE E1

Physical Characteristics for Various Graft Materials

| Sample | Max Load (Pounds Force) | % Strain at Max Load | % Strain at Break |
|---|---|---|---|
| Knitted Dacron Grafts | 42 ± 9 | 60 ± 24 | 60 |
| Nanofibrous Dacron | 3.7 ± 0.9 | 55 ± 8 | 62 ± 3 |
| ESDC Grafts | 3.4 ± 1.1 | 71 ± 10 | 91 ± 7 |

Figures 5A, 5B:
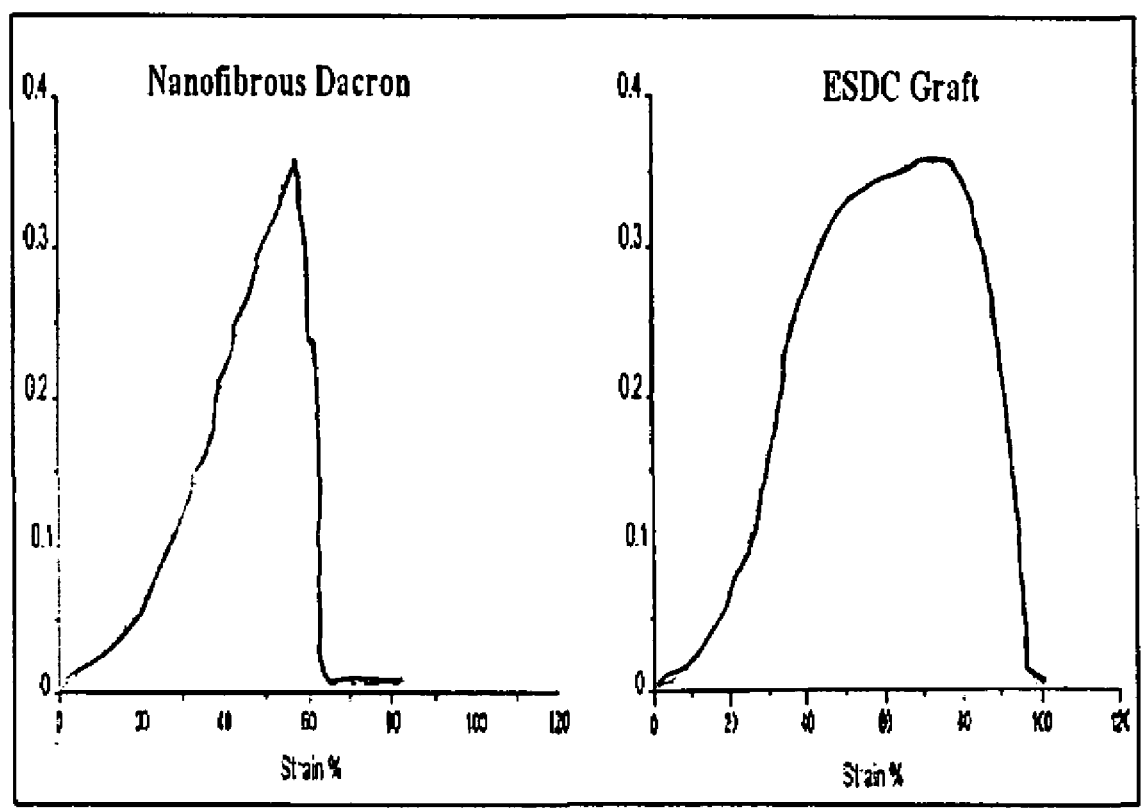
FIGS. 5A and 5B are graphs showing the marked differences between ESDC grafts and nanofibrous DACRON grafts under strain.

Moreover, while the breaking loads for the nanofibrous Dacron (3.7 pounds force) and the ESDC (3.4 pounds force) grafts were comparable, the curve shapes were significantly different. This is shown by the graphs of FIGS. 5A and 5B respectively.

The strain at break is higher for the ESDC grafts than the nanofibrous and knitted Dacron grafts, which equates to higher energy to break (i.e. increased toughness). The knitted Dacron graft had a much higher breaking load as expected due to the significantly greater wall thickness of the knitted Dacron graft. The other physical properties for the knitted graft such as the percent strain at break were similar to the nanofibrous Dacron graft indicating that break strength was directly related to wall thickness.

6. Determination of Collagen Fibers within ESDC Segment:

Amine presence within the novel ESDC segments as a result of collagen fiber formation was determined using CI Acid Red 1 (AR1) uptake, a methodology previously developed by our group (i). Briefly, a 500 ml stock solution of AR1 was prepared in MES buffer, pH 4.5 (MES). A working solution (50 mg/L) of AR1 was then prepared in MES. Nanofibrous Dacron and ESDC segments (0.5 cm length) were cut and weighed (n=4 segments/test group). Working AR1 solution (4 ml) was added to each segment and incubated overnight at room temperature on the inversion mixer. The segments were removed and placed into wash solution of MES buffer for one hour. Segments were then grossly observed for color uptake and photographed. Absorbance of the AR1 solutions pre- and post-segment exposure was also measured via spectrophotometer at 530 nm. Reflectance from the AR1-exposed nanofibrous Dacron and ESDC surfaces was measured using a Vistavision optical microscope with Ocean Optics fiber optic cable spectrophotometer.

Figure 6A:
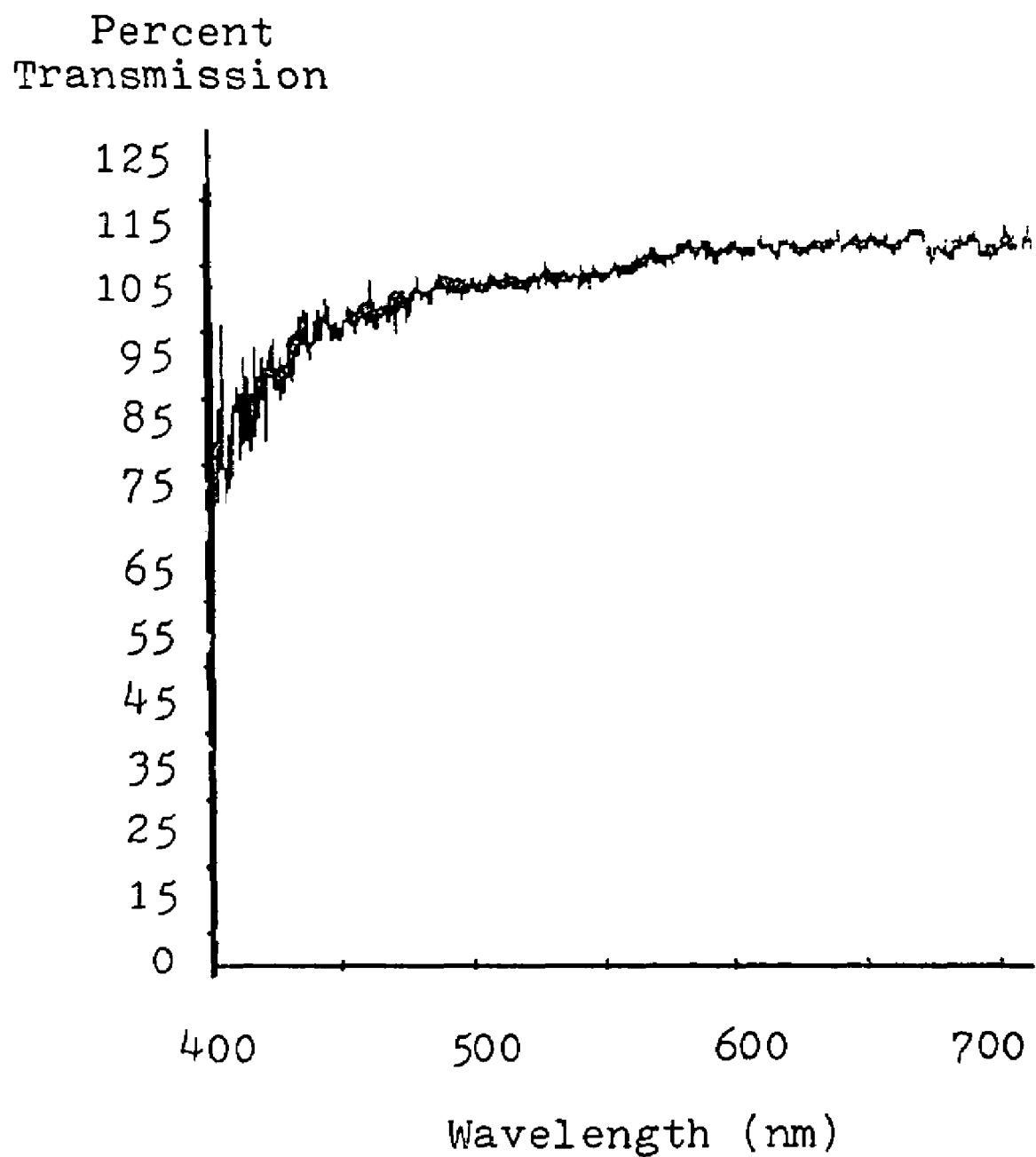
FIGS. 6A and 6B are graphs showing the marked differences in AR1 dye uptake between ESDC grafts and nanofibrous DACRON grafts.
Figure 6B:
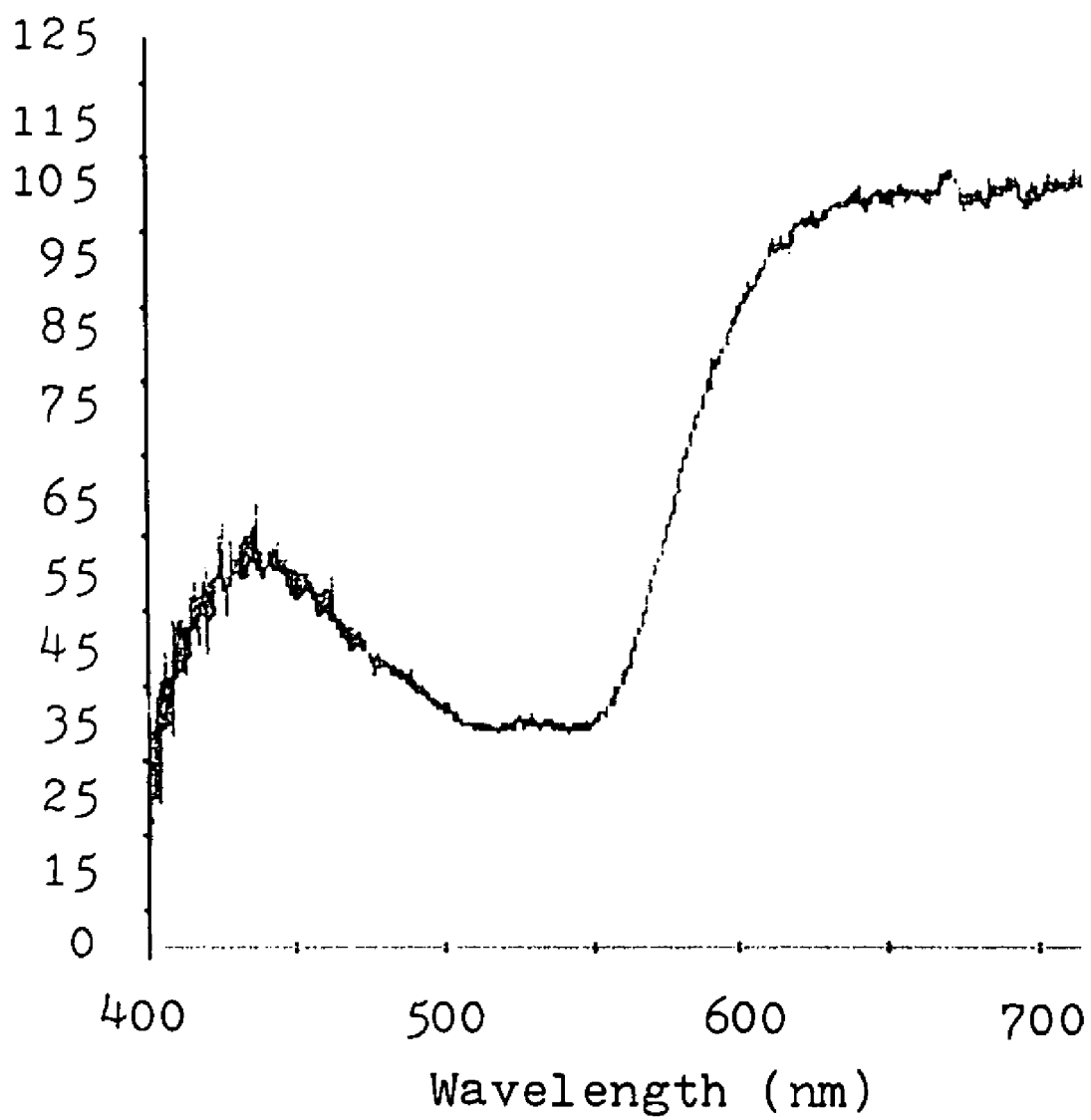

Results:

Exposure of the ESDC samples to AR1 showed significant dye uptake as compared to the nanofibrous Dacron controls which had no gross AR1 uptake, as shown by FIGS. 6A and 6B respectively. This was confirmed by the spectrophotometry studies which showed AR1 uptake by the ESDC segments corresponded to 1.6±0.3 nmoles AR1/mg segment weight. The nanofibrous Dacron controls had no measurable AR1 uptake.

Reflective measurement of nanofibrous Dacron and ESDC grafts post-AR1 dyeing also confirmed a strong uptake of AR1 on ESDC grafts as indicated by a significant reduction in percent transmission, as shown by FIG. 6. No AR1 uptake was evident on the nanofibrous Dacron control samples.

Experimental Series B: Immobilization of rHir and VEGF to ESDC Graft (ESDC-rHir- VEGF)

Methodology:

ESDC grafts were cut into 0.5 cm length segments and weighed (n=4 segments/test group, 2 groups). A stock 50 mM sodium bicarbonate buffer solution (pH 8.5) was utilized. A 20 mg/ml solution of Traut's reagent was prepared in the bicarbonate buffer and 2 ml was added to one set of ESDC segments in 5 ml borosilicate glass test tubes. To the other set, 2 ml of bicarbonate buffer was added. All segment sets were then reacted for 1 hour on the inversion mixer at room temperature. Within 20 minutes of completion, a 431 µM $^{125}$I-rHir solution (containing 33% radiolabelled $^{125}$I-rHir using Iodobeads) was prepared. A 23.8 µM $^{131}$I-VEGF solution (containing 25% radiolabelled $^{131}$I-VEGF using Iodobeads) was also prepared. The $^{125}$I-rHir solution was reacted with sulfo-SMCC in a 1:2 molar ratio. Simultaneously, $^{131}$I-VEGF was reacted with sulfo-SMCC in a 1:2 molar ratio. Both proteins were reacted for 20 minutes at 37° C. followed by purification via gel filtration. The $^{125}$I-rHir-SMCC solution was brought to a final concentration of 71.8 µM and $^{131}$I-VEGF-SMCC was brought to a final concentration of 4.76 µM.

$^{131}$I-VEGF-SH (2 ml) was exposed first to the control and test ESDC segments followed immediately by addition of 2 ml of $^{125}$I-rHir-SMCC. These segments were incubated for 3 hours at room temperature on an inversion mixer. Segments were then removed, followed by washing and sonication for 5 minutes (X4) in PBS with 9% Tween 20, replacing the wash buffer between sonications. Segments with non-specifically bound (ESDC+$^{125}$I-rHir-SMCC/$^{131}$I-VEGF-SMCC) and covalently bound (ESDC-S-SMCC-$^{125}$I-rHir/$^{131}$I-VEGF) $^{125}$I-rHir/$^{131}$I-VEGF were then gamma counted using an Iso-Data 100 dual channel gamma counter. Utilizing the specific activity, the amount of $^{125}$I-rHir and $^{131}$I-VEGF bound (ng) per weight of graft segment (mg) was determined.

Figure 7:
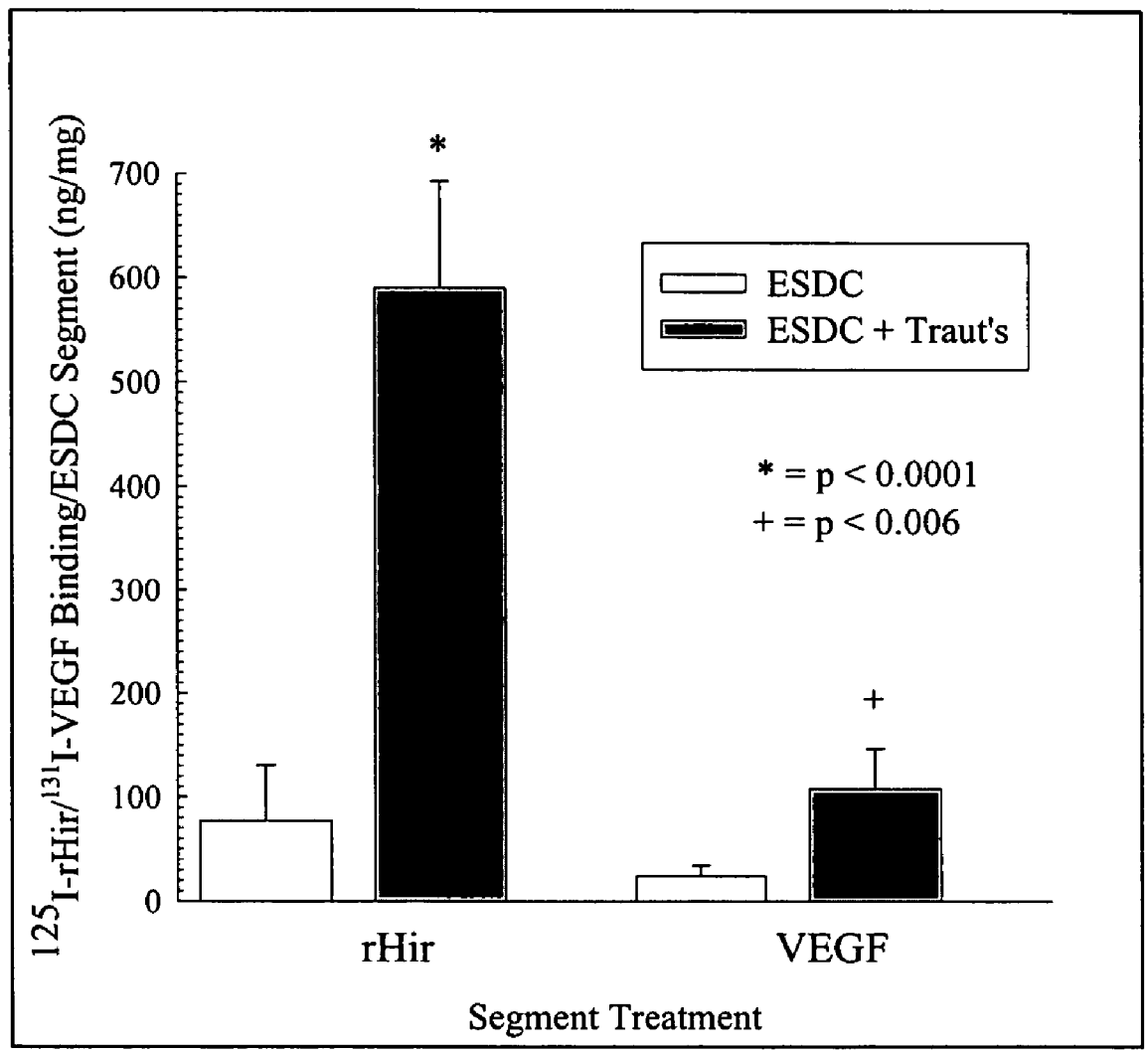
FIG. 7 is a graph showing the marked differences in rHir and VEGF binding for ESDC grafts in the presence and absence of Traut's reagent.

Results:

Covalent linkage of $^{125}$I-rHir to the ESDC surface (590±103 ng/mg) was 7.7 fold greater than the controls (77±53 ng/mg, p<0.0001), as shown by the graph of FIG. 7. Covalent immobilization of $^{131}$I-VEGF (108±38 ng/mg) was also significantly greater (4.5 fold) than the control ESDC segments (24±10 ng/mg, p<0.006). These stringent controls were exposed to all the experimental conditions of the test segments with the exception of eliminating the Traut's reagent reaction.

Thus, these results demonstrate the specificity of the $^{125}$I-rHir/$^{131}$I-VEGF for the Traut's reagent on the ESDC surface. The concentration of these surface bound proteins should provide a significant localized biologic effect. For example, the amount of growth factor estimated to be necessary to maintain biologic activity is 1 femtomole/cm$^2$. Our methodology renders a surface bound VEGF concentration well in excess of this threshold. Thus, $^{131}$I-VEGF-SMCC/$^{125}$I-rHir-SMCC concentrations applied to the ESDC surfaces will remain constant. The next step was to assess antithrombin activity of surface bound rHir.

Experimental Series C: Examination of Surface Antithrombin Properties Using a Chromogenic Assay Methods:

Thrombin inhibition by covalently bound $^{125}$I-rHir was determined using a chromogenic assay. Briefly, ESDC graft segments with non-specifically and covalently bound $^{125}$I-rHir were cut in the mid-sagittal plane to expose the luminal surface in half and gamma counted in order to determine surface bound $^{125}$I-rHir (n=2/graft type/test condition). Unmodified ESDC and ESDC graft segments with non-specifically bound $^{125}$I-rHir were treated in a similar fashion and will serve as controls. A thrombin stock solution (40 NIHU/ml) was utilized. From this stock solution, thrombin concentrations of 1, 2.5, 5 and 10 NIHU were prepared in borosilicate test tubes to a total volume of 2 ml with pre-warmed Tris buffer. Control and test segments were added to the respective thrombin solution and slightly mixed using an orbital shaker for 1 hour in a 37° C. air chamber. After incubation, 1 NIHU of thrombin from each test condition was aliquotted, placed into a 1 cm cuvette and brought up to a total volume of 1 ml with Tris buffer. The cuvettes were then equilibrated for 5 minutes at 37° C. in a Beckman spectrophotometer containing a thermocirculator. The reaction was started by the addition of 1 ml of 100 µM S-2238 with the change in absorbance per minute monitored at 15-second intervals for 3 minutes at 410 nm. Segments were then washed in PBS in 9% Tween 20 for 10 seconds and gamma counter again to determine rHir release from the surfaces.

Figure 8:
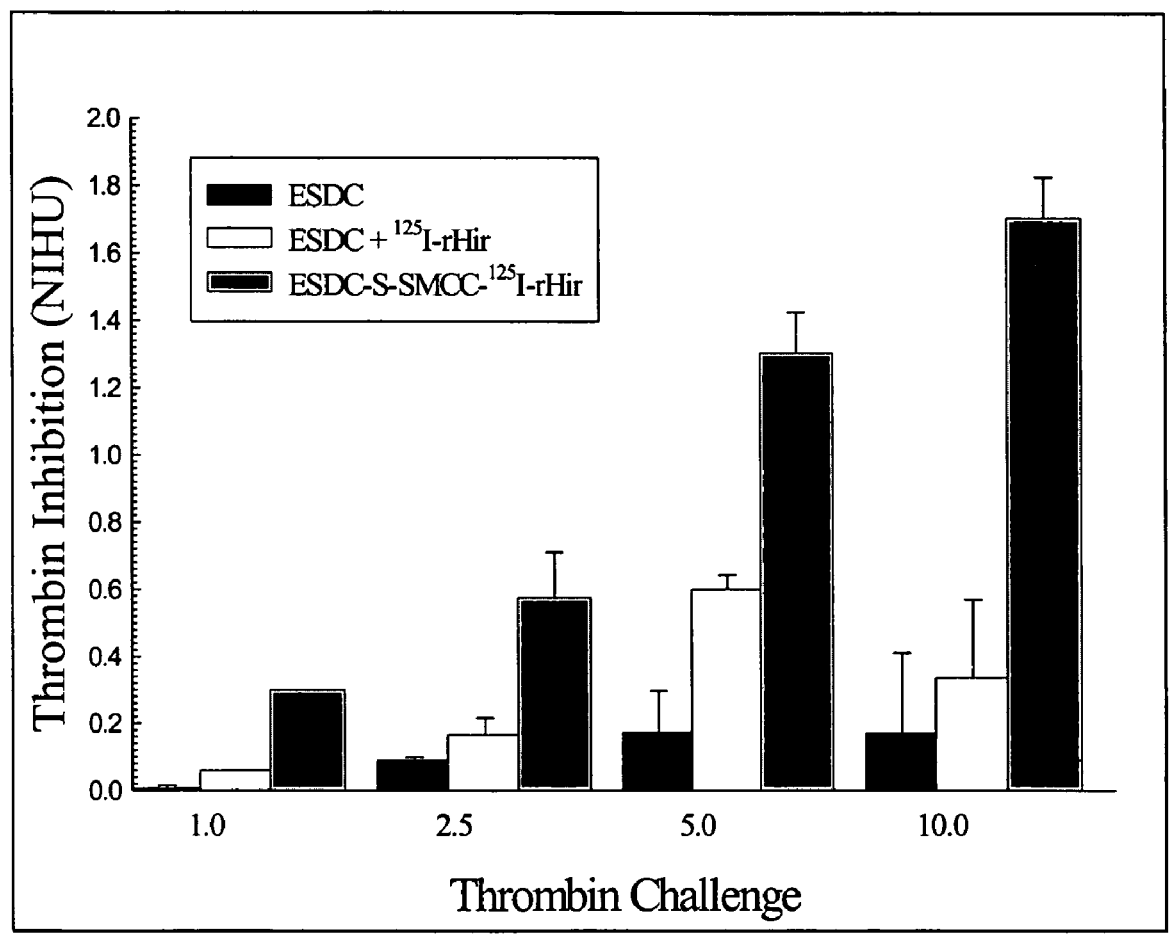
FIG. 8 is a graph showing the differences in thrombin inhibition among ESDC, ESDC+$^{125}$I-rHir, and ESDC-S-SMCC-$^{125}$I-rHir grafts.

Results:

Segments with both non-specific and covalently bound $^{125}$I-rHir inhibited thrombin at the four thrombin concentrations evaluated, as shown by the graph of FIG. 8. The ESDC segments with covalently bound $^{125}$I-rHir, however, inhibited significantly greater amounts (2-5 fold greater inhibition, p<0.05) of thrombin as compared to segments with non-specifically bound $^{125}$I-rHir. Maximum thrombin inhibition by non-specifically bound $^{125}$I-rHir was 0.6 NIHU. Surface bound $^{125}$I-rHir inhibited 1.71 NIHU, an amount lower than the projected surface antithrombin properties but at a minimum 2-fold greater than controls at the selected experimental conditions selected.

This difference can be attributed to a lack of interaction between thrombin and the surface bound $^{125}$I-rHir, which could be addressed by increasing reaction time and mixing parameters. This stringent control has not been employed in other studies, which typically uses the base material only as the control. Note also that $^{125}$I-rHir was not released from the surface of either non-specifically bound (9±2 ng/mg versus 8±2 ng/mg, p=0.40) or covalently bound (149±42 ng/mg versus 142±40 ng/mg, p=0.76) $^{125}$I-rHir segments after exposure to the various thrombin concentrations. Therefore, these results demonstrated that $^{125}$I-rHir covalently linked to the ESDC graft surface maintained biologic activity and was structurally stable even after interaction with thrombin.

Experimental Series D: Evaluation of Surface Mitogenic Properties Using an Alamar Blue Assay Methodology Human umbilical vein endothelial cells (HUVEC) were purchased from Cambrex (passage=4). HUVECs were grown to confluence in a 75 cm$^2$ vented flask using Kaighn's modified F12K complete medium containing 10% fetal bovine serum (FBS) and endothelial cell growth supplement HUVEC's were then grown in complete media (10% total FBS) for 24 hours. Cells were released from the culture flask surface using 6 ml trypsin, placed into 18 ml F12K with 10% FBS and counted using a bright-line hemacytometer. HUVEC concentration was adjusted to 40,000 cells/ml by dilution with medium prior to incubation with the various surfaces.

Circular segments of nanofibrous Dacron, ESDC with no modification and ESDC with covalently bound rHir/VEGF were utilized (n=4 segments/test group). All sets of segments were placed into sterile PBS containing 20% pen-strep antibiotic for 24 hours prior to use. These antibiotic-treated segments were set into a 24-well tissue culture plate and held in place using a proprietary ring seals. Trypsinized HUVEC's (0.5 ml) were then added to each well. Cells were allowed to incubate overnight in a 37° C. incubator with 5% CO$_2$. The next day, the F12K medium was suctioned off and 1.5 ml of a 10% Alamar Blue dye (in F12K medium with 10% FBS) added, an assay with which our group has extensive experience (ii). Alamar Blue was also added to 4 blank wells to serve as a negative control. This solution was incubated for 4 hours followed by removal of 1 ml into clear-sided fluorescence cuvettes. Solutions were then diluted 1:1 with F12K containing 10% FBS and fluorescence measured for each sample using a Perkin-Elmer LS-5B spectrofluorometer (excitation—506 nm, emission—590 nm, slit width—5). Difference in fluorescence intensity between the blank Alamar wells and segment-containing wells was determined.

Figure 9:
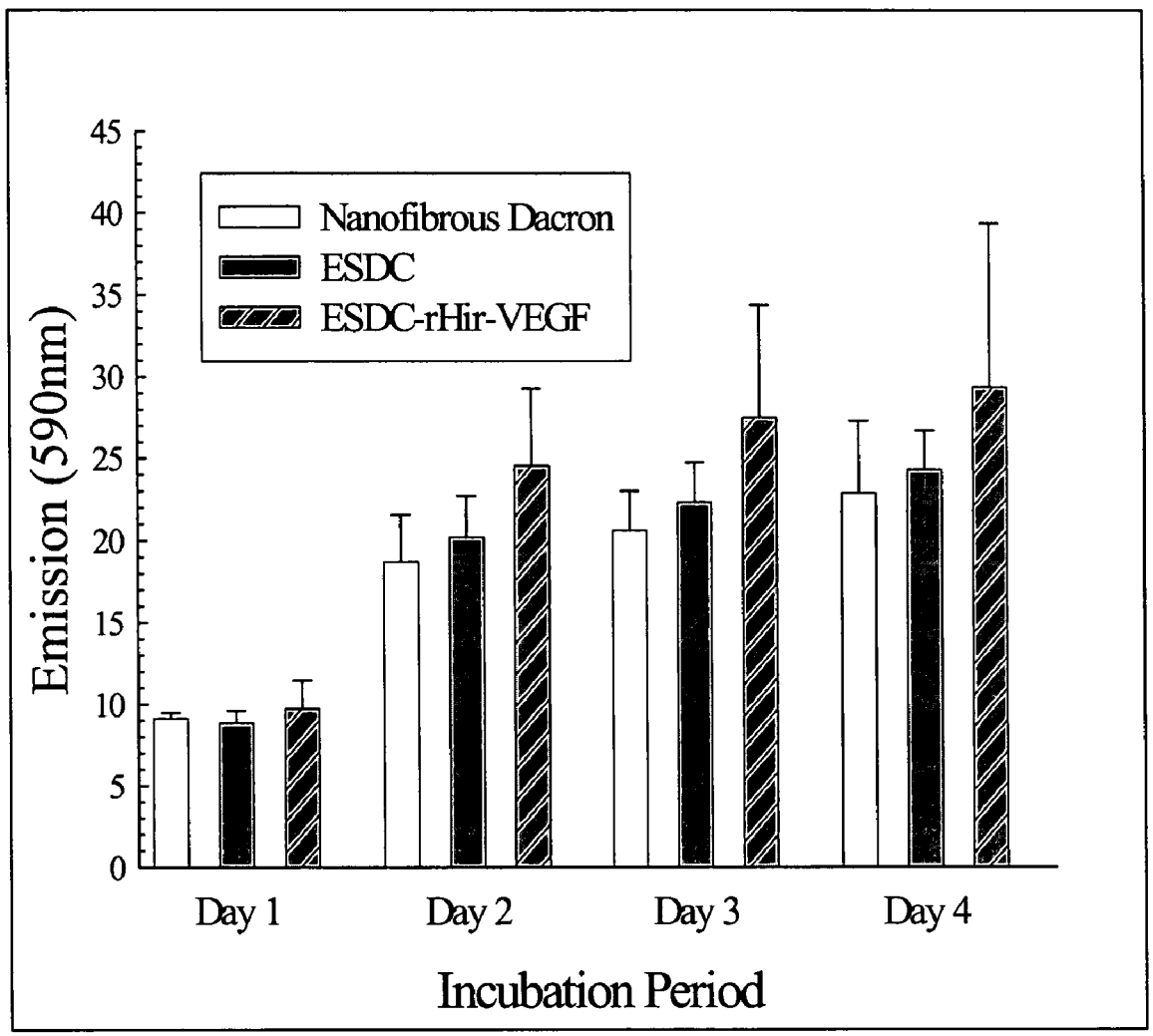
FIG. 9 is a graph showing the differences in fluorescence emissions among nanofibrous DACRON, ESDC, and ESDC-rHir-VEGF grafts.

Results:

The ESDC-rHir-VEGF segments had consistently greater HUVEC growth as indicated by fluorescence emission as compared to the ESDC and nanofibrous Dacron segments, as shown by the graph of FIG. 9. Assessment of the ESDC-rHir-VEGF surfaces for HUVEC growth properties demonstrated a consistent 19% and 26% greater growth than the ESDC and nanofibrous Dacron over the 4-day time period, although statistical significance was not reached due to the small sample size for cell culture. This small growth differential was anticipated since VEGF is not a potent endothelial cell mitogen such as Platelet-Derived Growth Factor (PDGF). However, unlike PDGF, VEGF, primarily expressed under hypoxic (non-optimal), conditions has endothelial cell specificity. These growth differences, which were under optimal growth conditions, have also been shown by other investigators when employing this growth factor in an unbound fashion. HUVECs coated directly onto the tissue culture plate, an optimum surface for cell attachment and growth, had the best growth over the 4-day period (66±16; data not shown). Thus, this study showed that surface bound VEGF maintained biologic activity and affected cellular activity even under optimum growth conditions.

Figure 10:
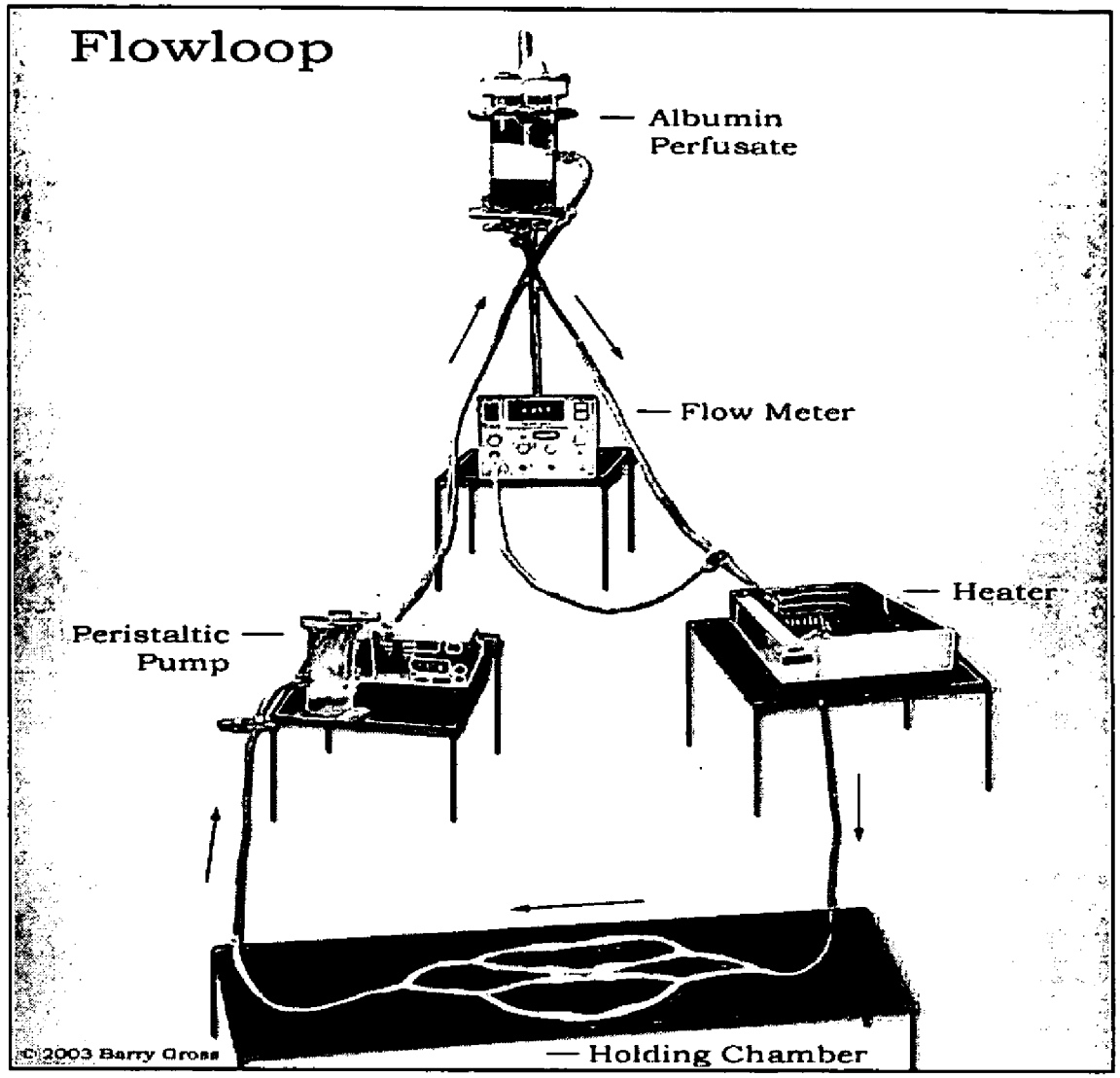
FIG. 10 is a visual image showing the apparatus used to assess surface rHir/VEGF stability under simulated arterial flow conditions.

Experimental Series E: Assessment of Surface rHir/VEGF Stability Under Simulated Arterial Flow Conditions Methods:

ESDC graft segments with either non-specifically or covalently bound $^{125}$I-rHir and $^{131}$I-VEGF were evaluated for surface protein stability upon subjection to static or simulated arterial flow conditions, using the apparatus shown by FIG. 10. ESDC grafts with either non-specifically or covalently bound $^{125}$I-rHir/$^{131}$I-VEGF were prepared as previously described (n=2 graft segments/test group/flow condition). Continuous monitoring of intraluminal flow was provided by a Model FM501D Carolina Medical Electronics electromagnetic flowmeter.

The perfusate was comprised of 550 ml of a 5% albumin (physiologic protein concentration)/PBS solution containing 400 mg Ciprofloxacin. Each graft segment was gamma counted prior to placement into the chamber in order to determine the initial amount of bound protein. For the static conditions, one set of control and test ESDC graft segments was placed into 10 ml of the perfusate and placed at 37° C. For flow assessment, the other set of control and test ESDC grafts was placed into a holding chamber which was then inserted into the flow loop. Graft segments were perfused at a flow rate of 230 ml/min. Grafts were removed from the chamber at various early (60 and 240 minutes) and late (i.e. 1, 2, 4, 5, 6 and 7 days) time intervals and gamma counted in order to determine the respective protein remaining on the ESDC surface.

Figure 11:
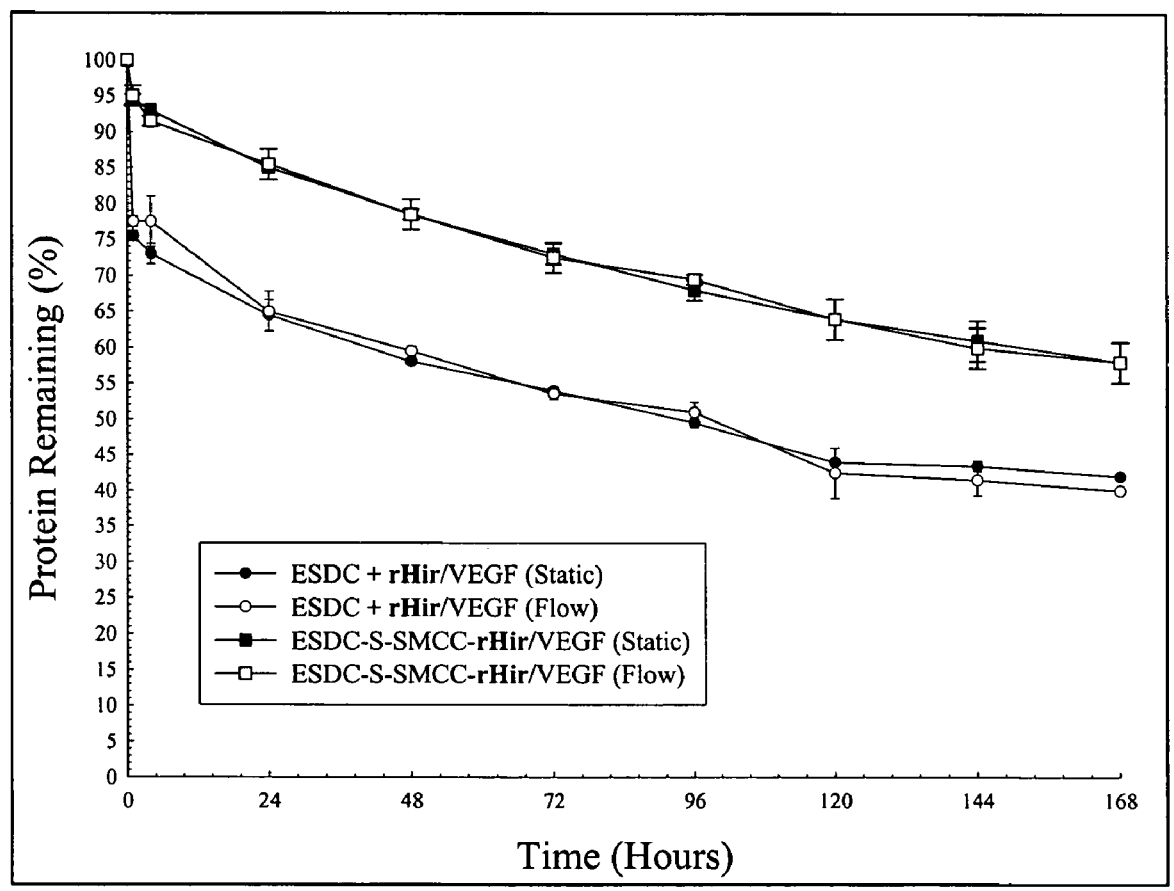
FIG. 11 is a first graph showing the differences in surface protein stability of grafts to static or arterial flow conditions.
Figure 12:
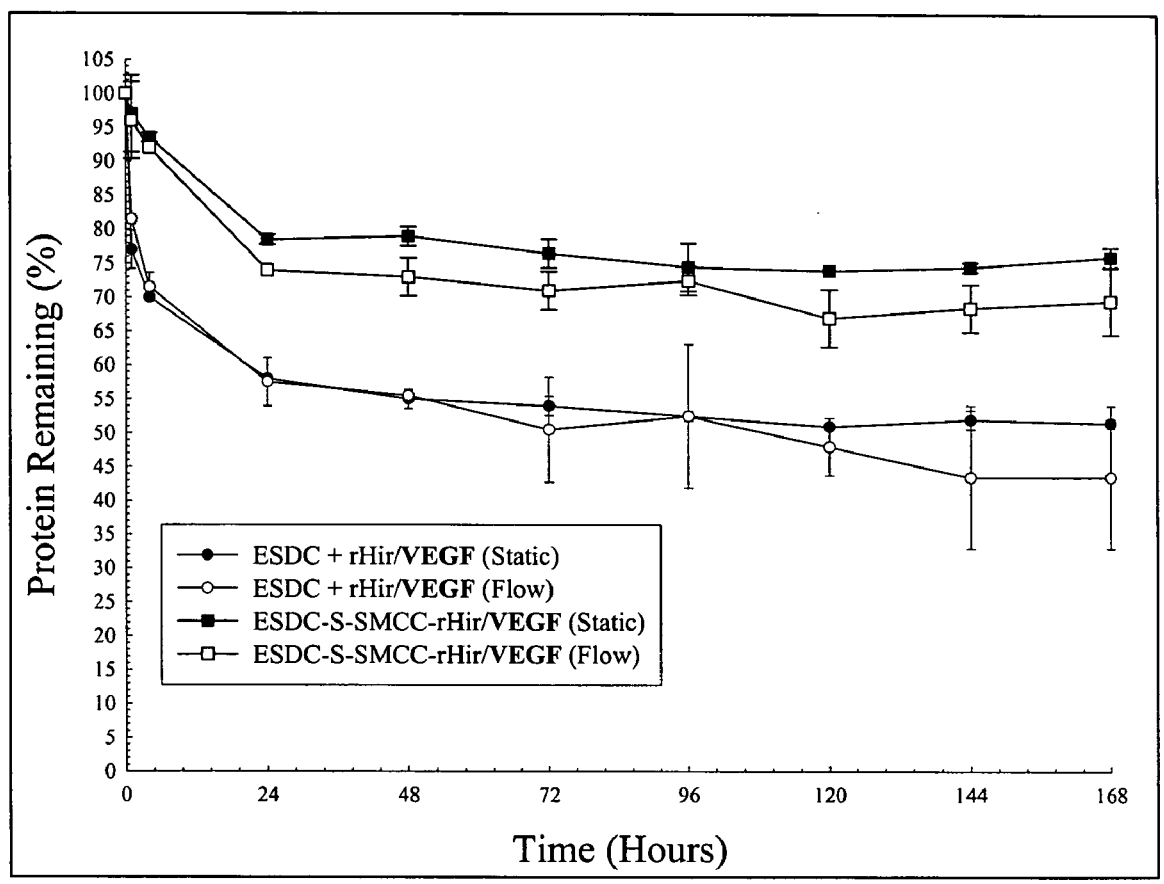
FIG. 12 is a second graph showing the differences in surface protein stability of grafts to static or arterial flow conditions.

Results:

ESDC graft segments with covalently bound $^{125}$I-rHir and $^{131}$I-VEGF had 58% and 70% protein remaining after exposure to arterial flow for 7 days, respectively, as shown by the graphs of FIGS. 11 and 12 respectively. This corresponds to 342 ng $^{125}$I-rHir/ESDC segment weight (mg) and 76 ng/ESDC segment weight (mg) $^{131}$I-VEGF remaining covalently bound to the surface at 7 days, amounts that would still provide a significant localized biologic effect.

In contrast, ESDC segments with non-specifically bound $^{125}$I-rHir and $^{131}$I-VEGF had 40% and 44% protein remaining after 7 days within the flow loop, respectively. This corresponded to 31 ng $^{125}$I-rHir/ESDC segment weight (mg) and 11 ng/ESDC segment weight (mg) $^{131}$I-VEGF remaining bound to the surface, 11 and 6.9 fold less protein remaining bound to that covalently immobilized onto the ESDC segments.

Loss of either protein from static or flow conditions was greatest within 24 hours, followed by a slow release over the subsequent 6 days. The amount of protein loss from the static flow segments with either non-specific or covalently bound $^{125}$I-rHir/$^{131}$I-VEGF was comparable to the segments exposed to arterial flow conditions. This study demonstrated that while there is acute release of $^{125}$I-rHir and $^{131}$I-VEGF from the ESDC surfaces, protein release was not flow induced. Additionally, a significant amount of $^{125}$I-rHir and $^{131}$I-VEGF remained immobilized after exposure to physiological protein concentrations as well as arterial flow conditions.

Experimental Series F: In Vivo Implantation of an ESDC Graft Into a Canine Femoral Artery Methods:

An adult mongrel canine (25 kg), which was designated for sacrifice by our collaborators at the Beth Israel Deaconess Medical Center, was sedated with Acepromazine (0.75 mg/kg) followed by induction with Pentothal (10-12 mg/lb). The animal was maintained on Halothane gas (0.5-1.5%). After draping and prepping, the right femoral artery was isolated. Following heparinization (100 U/kg), and under occlusion controls, an arteriotomy 1.5 times the internal diameter of the ESDC graft was performed.

The end of the graft was trimmed and an end-to-side anastomosis between the side of the artery and end of the ESDC was fashioned using running 6-0 Prolene suture. A similar anastomosis was performed on the distal aspect of the ipsilateral femoral artery. The intervening femoral artery was then ligated and transected, establishing a functional end-to-end anastomosis. Prior to completion of the anastomosis, the graft and vessel was de-aired to remove any air bubbles. Blood flow was then established through the graft, with flow permitted to continue for 2 hours. Gross observations such as suturability, blood permeation through the graft wall and weeping at the suture sites were made.

Figure 13:
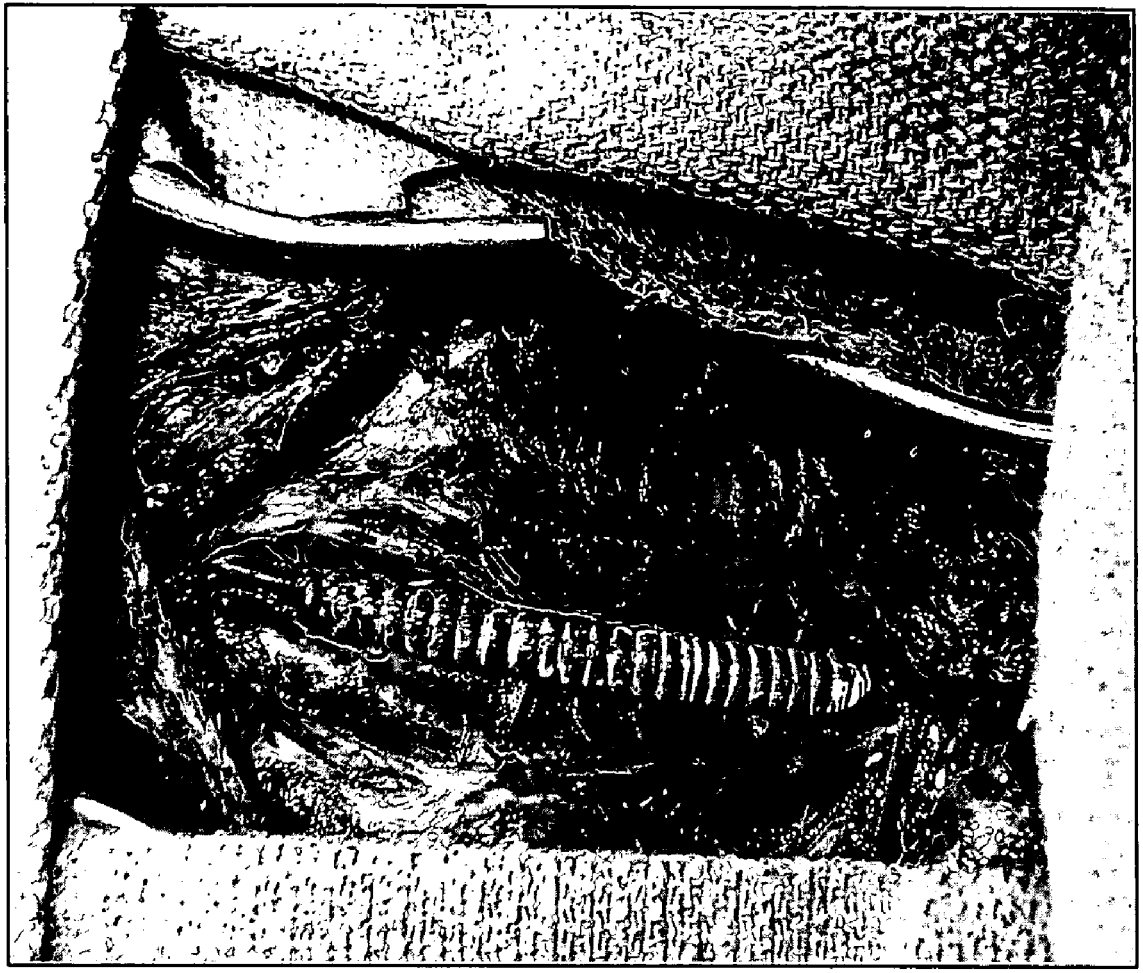
FIG. 13 is a visual image showing the suturing of an ESDC graft into a femoral artery in vivo.

Results:

Suturing of the ESDC graft into the femoral artery presented no adverse problems, as visually shown by FIG. 13. There was also no weeping around the suture sites after establishing blood flow through the graft. This result was promising since the blood remained heparinized throughout the study.

In this clinical implantation, heparin activity is typically reversed with protamine after establishing blood flow within the graft, thereby providing clotting factors to seal around the sutures and potential defects within a graft wall. No weeping at these sites showed excellent sealing properties of the graft after puncture. There was also no blood permeation through the graft wall through any point of the implantation period. This result validated our in vitro water permeation studies which showed low water permeation through the graft wall. Thus, this animal model study demonstrates that the ESDC graft can be implanted into the canine femoral arteries. The ESDC graft showed excellent suturability, no suture site weeping and no blood permeation through the graft wall, all properties that are desired for prosthetic vascular grafts.

VI. Importance of the Experiments and Empirical Data

The primary goal of the experiments was to fabricate a nanofibrous biocomposite vascular graft suitable for clinical applications in vivo. This goal has been successfully achieved.

It is therefore beneficial to note and summarize some of the major developments and accomplishments evidenced and factually demonstrated by the experimental design and the empirical data presented herein. Among these are the following:

1. Experimentally, solubilization of the synthetic polymer (DACRON) and the basement membrane protein (Type IV Collagen) into a single solution was accomplished using ice-cold HFIP in conjunction with constant mixing over a period of 48 hours. Use of HFIP at room temperature with mixing resulted in an inconsistent solubilization of the Dacron polymer chips, and therefore was not employed.

Once this reliable solubilization technique was employed, collagen concentrations within the polymer solution were varied. Collagen presence within this novel material was important for providing binding sites for protein attachment and for serving as a scaffold for endothelial cell attachment. AR1 uptake and reflectance studies showed that a collagen concentrations below 1% (w:v) had limited collagen content within the biocomposite material. In our previous studies, AR1 uptake directly correlated with accessible amine functional groups available for protein binding. Collagen concentrations ranging from 1.5% to 2.0% showed similar AR1 uptake. Due to similar AR1 uptake results as well as the cost for collagen, the 1.5% collagen concentration within the polymer solution was utilized.

After the desireable polymer concentration was determined, formation of the tubular ESDC structure was performed. Development of the self-contained, semi-automated electrospinning apparatus provided a controlled environment that eliminated many of the outside conditions (i.e. air flow, static discharge) adverse to consistent material formation. Variation of electrospinning time was one of the main parameters assessed. Electrospinning for 40 minutes at an applied voltage of 15 kV, gap distance of 15 cm and flow rate of 3 ml/hour resulted in excellent wall flexibility in the material. Increasing electrospinning time significantly increased the rigidity of the material. Conversely, electrospinning for shorter periods of time (1-15 minutes) provided a tubular structure without significant wall strength. Thus, these parameters were employed routinely for ESDC graft formation in these experiments.

2. One significant problem, which was expected, was the kinking of the graft wall at bend angles greater than 15°. This problem demonstrated the need for creating kink-resistant properties within the graft wall.

Originally, several different technologies were investigated for creating kink-resistance within the graft wall. The first attempt was incorporation of a DACRON reinforcement directly into the fabricated graft wall. Several different techniques—ranging from altering reinforcement diameter, reinforcement composition, coil distance, adhesion via solvent exposure and heat setting post-electrospinning—were examined. Each methodology resulted in a similar outcome, a separation of the two layers adjacent to the reinforcement. This undesirable result is attributed to stopping the electrospinning process in order to apply the reinforcement material. This time frame, albeit short, may have permitted the HFIP solvent to evaporate from the biocomposite material, resulting essentially in two grafts being formed.

The next attempt to create kink-resistance for the graft wall involved using a high temperature heat setting with no compression. While this methodology maintained wall integrity, wall flexibility was significantly impaired. The final method to create a kink-resistant wall employed using a low temperature heat set in conjunction with compression. This technique maintained wall integrity while still maintaining flexibility within the construct. Thus, this novel technology was employed exclusively for providing kink-resistance in the ESDC graft.

3. Assessment of the physical characteristics of the ESDC graft was the next objective of the experimental design. It was recognized that development of a graft-like structure without any tangible handling properties would render the graft useless.

Low water permeation (representative of blood permeation) and significant material tensile strength are the two essential physical characteristics required for all prosthetic grafts. Water permeation values below 100 ml/min/cm² have been shown to prevent blood seepage through the graft wall.

Water permeation for the ESDC grafts was 29 ml/min/cm², a value comparable to the clinically used, collagen-impregnated Hemashield® grafts. For tensile strength, the ESDC grafts showed the presence of yield point and the plastic flow, notably absent in the knitted and nanofibrous Dacron grafts. The strain at break is higher for the ESDC grafts than the nanofibrous and knitted Dacron grafts, which equates to higher energy to break resulting in increased toughness. The knitted Dacron graft had a much higher breaking load than the ESDC graft, as expected, due to the significantly greater wall thickness of the knitted graft. The other physical properties for the knitted graft such as the percent strain at break were similar to the ESDC graft indicating that break strength was directly related to wall thickness.

Currently used Dacron and ePTFE grafts have physical properties that far exceed the arterial vessels they are sewn into. The rationale for this excess is unclear since it is postulated that one reason for graft failure is compliance mismatch between the relatively stiff, bulky graft and the native vessel. Thus, this novel thin-walled graft had water permeation values comparable to clinically-utilized Dacron and ePTFE prosthetic grafts while maintaining excellent handling characteristics.

4. Immobilization of bioactive agents onto the ESDC surface was the next step. rHir and VEGF were then covalently bound simultaneously to the ESDC surface. Utilizing the established crosslinking technology, immobilization of rHir and VEGF to the ESDC surface was 7.7 and 4.5 fold, respectively greater than ESDC controls in which only one step (Traut's reagent incubation with the ESDC surface) was eliminated. These results demonstrate the specificity of the rHir/VEGF for the Traut's reagent on the ESDC surface. Furthermore, evaluation of ESDC with covalently bound $^{125}$I-rHir for surface thrombin inhibition properties, using a chromogenic assay which measured residual thrombin activity, showed significantly greater thrombin inhibition (2-5 fold) over ESDC segments with non-specifically bound rHir. Additionally, $^{125}$I-rHir was structurally stable even after interaction with thrombin. Assessment of the ESDC-rHir-VEGF surfaces for HUVEC growth properties, using an Alamar Blue assay, demonstrated a consistent 19% and 26% greater growth than the ESDC and nanofibrous Dacron graft segments over the 4-day time period. This small growth differential was expected since VEGF is not a potent endothelial cell mitogen such as Platelet-Derived Growth Factor (PDGF). However, VEGF, which is primarily expressed under hypoxic (non-optimal) conditions, has endothelial cell specificity. These growth differences, which were determined under optimal growth conditions, have also been shown by other investigators when employing this growth factor in an unbound fashion. Overall, these surface bound agents showed biological activity using these specific in vitro assays.

5. ESDC-$^{125}$I-rHir-$^{131}$I-VEGF graft segments were evaluated for surface protein stability upon subjection to static or simulated arterial flow conditions. This system was designed to mimic some of the conditions of the vascular environment (i.e. flow rate, temperature, protein concentration). The flow rate selected for this study (230 ml/minute) was slightly higher than the flow conditions this surface would normally encounter once implanted (150-200 ml/minute). This experimentally-controlled scenario provided a greater challenge to these surface bound proteins. Even under these conditions, the immobilized proteins had excellent surface stability upon exposure to arterial flow conditions for the 7 day period. Additionally, the amount of protein remaining on the ESDC surface would still provide a significant localized biologic effect.

6. Lastly, in vivo implantation of this novel ESDC graft into an arterial grafting model was also accomplished. This in vivo experimental study was initiated as a consequence of the significant progress made in the in vitro studies, in addition to evaluating the potential for clinically implanting this graft.

The ESDC graft, which was implanted in an acute (2 hours) fashion into the femoral artery of a canine, showed excellent suture retention with no blood permeation through the graft wall or suture sites throughout this implantation period, a crucial period for structural analysis of a prosthetic graft. Thus, successful implantation of the ESDC graft provides the probative evidentiary foundation upon which the various clinical applications will be based.

The present invention is not to be restricted in form nor limited in scope except by the claims appended hereto.

What we claim is:

1. A small diameter textile conduit fabricated via an electrospinning perfusion process and useful as a tangible workpiece for the manufacture of a prosthetic vascular graft construct, said textile conduit comprising:

a non-perforated hollow tube which has been fabricated via an electrospinning perfusion process and which exists as an electrospun nanofibrous biocomposite material generated from a fluid admixture comprised of at least one biodurable synthetic substance and at least one extracellular matrix protein which has been subjected to an electric current, said electrospun hollow tube presenting a single nanofibrous material wall comprised of discrete fibers wherein said biodurable synthetic substance is present primarily as $10^{-8}$ meter diameter fibers and said extracellular matrix protein is present primarily as $10^{-9}$ meter diameter fibers, having two open ends and an internal lumen less than about 6 millimeters in diameter, and providing an internal wall surface biocompatible for the conveyance of blood through said internal lumen.

2. The textile conduit recited in claim 1 wherein said biodurable synthetic substance of said nanofibrous biocomposite material is a polymeric composition.

3. The textile conduit recited in claim 1 wherein said biodurable synthetic substance of said nanofibrous biocomposite material is a polymer selected from the group consisting of polyethylene terephthalate, nylon, polyurethane, polyglycolic acid, polyamides, polytetrafluoroethylene, polyesters, and mixtures of these substances.

4. The textile conduit recited in claim 1 wherein said biodurable synthetic substance of said nanofibrous biocomposite material is a compound selected from the group consisting of an acetate, triacetate, acrylic, acrylonitrile, aramid, modacrylic, olefin, propylene, ethylene, and saran.

5. The textile conduit recited in claim 1 wherein said extracellular matrix protein of said nanofibrous biocomposite material is one selected from the group consisting of a collagen, an elastin, fibrinogen, and fibrin.

6. A prosthetic vascular graft construct useful as a synthetic blood vessel in-vivo, said prosthetic vascular graft construct comprising:

an electrospun textile conduit comprised of a non-perforated hollow tube which has been fabricated via an electrospinning perfusion process and which exists as an electrosoun nanofibrous biocomposite material generated from a fluid admixture comprising at least one biodurable synthetic substance and at least one extracellular matrix protein which has been subjected to an electric current, said electrospun textile conduit presenting a single nanofibrous material wall comprised of discrete fibers wherein said biodurable synthetic substance is present primarily as $10^{-8}$ meter diameter fibers and said extracellular matrix protein is present primarily as $10^{-9}$ meter diameter fibers, having two open ends and an internal lumen less than about 6 millimeters in diameter, and providing an internal wall surface biocompatible for the conveyance of blood through said internal lumen; and at least one pre-chosen biologically active compound which is permanently bound to said wall surfaces of said electrospun textile conduit, said bound compound having recognized biologically active properties for mediating the conveyance of blood through said internal lumen of said electrospun textile conduit.

7. A prosthetic vascular graft construct useful as a synthetic blood vessel in-vivo, said prosthetic vascular graft construct comprising:

an electrospun textile conduit comprised of a non-perforated hollow tube which has been fabricated via an electrospinning perfusion process and which exists as an electrospun nanofibrous biocomposite material generated from a fluid admixture comprising at least one biodurable synthetic substance and at least one extracellular matrix protein which has been subjected to an electric current, said electrospun textile conduit presenting a single nanofibrous material wall comprised of discrete fibers wherein said biodurable synthetic substance is present primarily as $10^{-8}$ meter diameter fibers and said extracellular matrix protein is present primarily as $10^{-9}$ meter diameter fibers, having two open ends and an internal lumen less than about 6 millimeters in diameter, and providing an internal wall surface biocompatible for the conveyance of blood through said internal lumen;

at least one bifunctional linking agent joined to said internal wall surface of said electrospun textile conduit; and at least one pre-chosen biologically active compound which is permanently bound by said joined bifunctional linking agent to said internal wall surface of said electrospun textile conduit, said bound compound having recognized biologically active properties for mediating the conveyance of blood through said internal lumen of said electrospun textile conduit.

8. The prosthetic vascular graft construct recited in claim 6 or 7 wherein said biodurable synthetic substance of said nanofibrous biocomposite material is a polymer selected from the group consisting of polyethylene terephthalate, nylon, polyurethane, polyglycolic acid, polyamides, polytetrafluoroethylene, polyesters, and mixtures of these substances.

9. The prosthetic vascular graft construct recited in claim 6 or 7 wherein said biodurable synthetic substance of said nanofibrous biocomposite material is a compound selected from the group consisting of an acetate, triacetate, acrylic, acrylonitrile, aramid, modacrylic, olefin, propylene, ethylene, and saran.

10. The prosthetic vascular graft construct recited in claim 6 or 7 wherein said extracellular matrix protein of said nanofibrous biocomposite material is one selected from the group consisting of a collagen, an elastin, fibrinogen, and fibrin.

11. The prosthetic vascular graft construct recited in claim 6 or 7 wherein said biologically active compound is selected from the group consisting of proteins and proteinaceous matter.

12. The prosthetic vascular graft construct recited in claim 11 wherein said biologically active compound is a blood anti-coagulation protein.

13. The prosthetic vascular graft construct recited in claim 11 wherein said biologically active compound is a growth factor.

14. The prosthetic vascular graft construct recited in claim 11 wherein said biologically active compound is a cytokine.

15. The prosthetic vascular graft construct recited in claim 11 wherein said biologically active compound is a lectin.

16. The prosthetic vascular graft construct recited in claim 11 wherein said biologically active compound is selected from the group consisting of glycoproteins and protoglycans.

17. The prosthetic vascular graft construct recited in claim 6 or 7 wherein said biologically active compound is an oligonucleotide.

18. The prosthetic vascular graft construct recited in claim 6 or 7 wherein said biologically active compound is selected from the group consisting of saccharides and polysaccharides.

19. The prosthetic vascular graft construct recited in claim 7 wherein said bifunctional linking agent is selected from the group consisting of sulfosuccinimidyl 4-(N-maleimidomethyl)cyclohexane-1-carboxylate (sulfo-SMCC), succinimidyl 4-(N-maleimidomethyl)cyclohexane-1-carboxylate (SMCC); Nsuccinimidyl-3-(2-pyridyldithio)propionate (SPpP), sulfosuccinimidyl 2-(7-azido-4-methylcoumarin-3-acetamide)ethyl-1,3'-dithiopropionate (SAED), 1-ethyl-3-(dimethylaminopropyl)-carbodiimide HCl (EDC), and Traut's reagent (2-iminothiolane hydrochloride).

20. An electrospinning perfusion method for making a textile conduit, said method comprising the steps of:

erecting an electrospinning perfusion assembly comprised of a rotating mandrel which can be set at a selected rotation speed, a perfusion instrument which can be set at a specified liquid flow rate, and an electrical coupling for controlling and coordinating the actions of said perfusion instrument upon said rotating mandrel;

preparing a fluid mixture comprised of at least one biodurable synthetic substance, at least one kind of extracellular matrix protein, and an organic liquid carrier;

introducing said prepared fluid mixture to said perfusion instrument of said assembly;

perfusing said fluid admixture onto said rotating mandrel for a predetermined time such that an electrospun textile conduit is fabricated, wherein said electrospun textile conduit (i) is an elongated, hollow single-wall tube of determinable dimensions which is formed of an electrospun nanofibrous biocomposite material comprised of discrete fibers wherein said biodurable synthetic substance is present primarily as $10^{-8}$ meter diameter fibers and said extracellular matrix protein is present primarily as $10^{-9}$ meter diameter fibers, (ii) has two open ends and an internal lumen less than about 6 millimeters in diameter, (iii) presents a discrete interior wall surface and an exterior wall surface, and (iv) is biocompatible for the conveyance of blood.

21. A method for making a textile conduit useful as an antecedent workpiece in the manufacture of a prosthetic vascular graft construct, said method comprising the steps of:

preparing a fluid mixture comprised of at least one biodurable synthetic substance, at least one kind of extracellular matrix protein, and an organic liquid carrier;

subjecting said prepared fluid mixture to an electrospinning perfusion process; and fabricating an elongated, hollow single-wall textile conduit via said electrospinning perfusion process which is formed of a an electrospun nanofibrous biocomposite material comprised of discrete fibers wherein said biodurable synthetic substance is present primarily as $10^{-8}$ meter diameter fibers and said extracellular matrix protein is present primarily as $10^{-9}$ meter diameter fibers, whereby said fabricated textile conduit (i) has two open ends and an internal lumen less than about 6 millimeters in diameter, and (ii) presents a discrete interior wall surface and an exterior wall surface, and (iii) is biocompatible for the conveyance of blood through said internal lumen.

22. The method for making the textile conduit recited in claim 20 or 21 wherein said organic liquid carrier of said fluid mixture is selected from the group consisting of hexafluoroisopropanol, dimethylformamide, dimethylsulfoxide, acetonitrile, acetone, hexamethylphosphoric triamide, N,N-diethylacetamine, and N-methylpyrrolidinone.

23. The method for making the textile conduit recited in claim 20 or 21 wherein said biodurable synthetic substance of said fluid mixture is a polymer.

24. The method for making the textile conduit recited in claim 20 or 21 wherein said biodurable synthetic substance of said fluid mixture is a polymer selected from the group consisting of polyethylene terephthalate, nylon, polyurethane, polyglycolic acid, polyamides, polytetrafluoroethylene, polyesters, and mixtures of these substances.

25. The method for making the textile conduit recited in claim 20 or 21 wherein said biodurable synthetic substance of said fluid mixture is a compound selected from the group consisting of an acetate, triacetate, acrylic, acrylonitirile, aramid, modacrylic, olefin, propylene, ethylene, and saran.

26. The method for making the textile conduit recited in claim 20 or 21 wherein said extracellular matrix protein of said fluid mixture is one selected from the group consisting of a collagen and an elastin.

27. A method for making a prosthetic vascular graft construct, said method comprising the steps of:

preparing a fluid mixture comprised of at least one biodurable synthetic substance, at least one extracellular matrix protein, and an organic liquid carrier;

subjecting said prepared fluid mixture to an electrospinning perfusion process;

fabricating a textile conduit via said electrospinning perfusion process as an elongated, hollow single-wall tube formed of an electrospun nanofibrous biocomposite material comprised of discrete fibers wherein said biodurable synthetic substance is present primarily as $10^{-8}$ meter diameter fibers and said extracellular matrix protein is present primarily as $10^{-9}$ meter diameter fibers, whereby said fabricated textile conduit (i) has two open ends and an internal lumen less than about 6 millimeters in diameter, and (ii) presents a discrete interior wall surface and an exterior wall surface, and (iii) is biocompatible for the conveyance of blood through its internal lumen;

combining at least one bifunctional linking agent and at least one pre-chosen biologically active compound to generate an intermediate complex, said pre-chosen compound having recognized biologically active properties for mediating the conveyance of blood in-vivo; and reactively adding said intermediate complex to said fabricated textile conduit whereby said active compound of said intermediate complex becomes permanently bound to said wall surfaces of said fabricated textile conduit, and wherein said permanently bound compound retains its recognized biologically active properties for mediating the conveyance of blood in-vivo.

28. A method for making a prosthetic vascular graft construct, said method comprising the steps of:

obtaining a textile conduit which has been fabricated via an electrospinning perfusion process and which is an elongated, hollow single-wall tube formed of an electrospun nanofibrous biocomposite material comprised of a mixture of discrete fibers, where a portion of said fibers are composed of a biodurable synthetic substance present primarily as $10^{-8}$ meter diameter fibers and another portion of said fibers are composed of an extracellular matrix protein present primarily as $10^{-9}$ meter diameter fibers, and wherein said fabricated textile conduit (i) has two open conduit ends and an internal lumen less than about 5 millimeters in diameter, (ii) presents a discrete interior wall surface and an exterior wall surface, and (iii) is biocompatible for the conveyance of blood through its internal lumen;

combining at least one bifunctional linking agent and at least one pre-chosen biologically active compound to generate an intermediate complex, said pre-chosen compound having recognized biologically active properties for mediating the conveyance of blood in-vivo; and reactively adding said intermediate complex to said fabricated textile conduit whereby said active compound of said intermediate complex becomes permanently bound to said wall surfaces of said fabricated textile conduit, and wherein said permanently bound compound retains its recognized biologically active properties for mediating the conveyance of blood in-vivo.

29. The method for making the prosthetic vascular graft construct recited in claim 27 wherein said organic liquid carrier of said fluid mixture is selected from the group consisting of hexafluoroisopropanol, dimethylformamide, dimethylsulfoxide, acetonitrile, acetone, hexamethylphosphoric triamide, N,N-diethylacetamine, and N-methylpyrrolidinone.

30. The method for making the prosthetic vascular graft construct recited in claim 27 wherein said biodurable synthetic substance of said fluid admixture is a polymer.

31. The method for making the prosthetic vascular graft construct recited in claim 27 wherein said biodurable synthetic substance of said fluid mixture is a polymer selected from the group consisting of polyethylene terephthalate, nylon, polyurethane, polyglycolic acid, polyamides, polytetrafluoroethylene, polyesters, and mixtures of these substances.

32. The method for making the prosthetic vascular graft construct recited in claim 27 wherein said biodurable synthetic substance of said fluid admixture is a compound selected from the group consisting of an acetate, triacetate, acrylic, acrylonitrile, aramid, modacrylic, olefin, propylene, ethylene, and saran.

33. The method for making the prosthetic vascular graft construct recited in claim 27 wherein said extracellular matrix protein of said fluid mixture is one selected from the group consisting of a collagen, an elastin, fibrinogen, and fibrin.

34. The method for making the prosthetic vascular graft construct recited in claim 27 or 28 wherein said bifunctional linking agent is selected from the group consisting of sulfo-succinimidyl 4-(N-maleimidomethyl)cyclohexane-1-carboxylate (sulfo-SMCC), succinimidyl 4-(N-maleimidomethyl)cyclohexane-1-carboxylate (SMCC); Nsuccinimidyl-3-(2-pyridyldithio)propionate (SPDP), sulfosuccinimidyl 2-(7-azido-4-methylcoumarin-3-acetamide) ethyl-1,3'-dithiopropionate (SAED), 1-ethyl-3-(dimethylaminopropyl)-carbodiimide HCl (EDC), and Traut's reagent (2-iminothiolane hydrochloride).

35. The method for making the prosthetic vascular graft construct recited in claim 27 or 28 wherein said biologically active compound is selected from the group consisting of proteins and proteinaceous matter.

36. The method for making the prosthetic vascular graft construct recited in claim 35 wherein said biologically active compound is a blood anti-coagulation protein.

37. The method for making the prosthetic vascular graft construct recited in claim 35 wherein said biologically active compound is a growth factor.

38. The method for making the prosthetic vascular graft construct recited in claim 35 wherein said biologically active compound is a cytokine.

39. The method for making the prosthetic vascular graft construct recited in claim 35 wherein said biologically active compound is a lectin.

40. The method for making the prosthetic vascular graft construct recited in claim 27 or 28 wherein said biologically active compound is selected from the group consisting of glycoproteins and protoglycans.

41. The method for making the prosthetic vascular graft construct recited in claim 27 or 28 wherein said biologically active compound is an oligonucleotide.

42. The method for making the prosthetic vascular graft construct recited in claim 27 or 28 wherein said biologically active compound is selected from the group consisting of saccharides and polysaccharides.

* * * * *

UNITED STATES PATENT AND TRADEMARK OFFICE
CERTIFICATE OF CORRECTION

| | |
|---|---|
| PATENT NO. | : 7,413,575 B2 |
| APPLICATION NO. | : 11/211935 |
| DATED | : August 19, 2008 |
| INVENTOR(S) | : Matthew D. Phaneuf, Philip J. Brown and Martin J. Bide |

It is certified that error appears in the above-identified patent and that said Letters Patent is hereby corrected as shown below:

In the Specification

Column 1 line 3, add the following paragraph before the paragraph entitled PRIORITY CLAIM:

"GOVERNMENT LICENSE RIGHTS
This invention was made with government support under Contract No. R44 HL074771 awarded by Small Business Innovation Research (SBIR). The government has certain rights in the invention."

Signed and Sealed this
Eighteenth Day of August, 2015

Michelle K. Lee
*Director of the United States Patent and Trademark Office*